(12) United States Patent
Petit et al.

(10) Patent No.: US 10,947,519 B2
(45) Date of Patent: Mar. 16, 2021

(54) YEAST STRAINS CO-EXPRESSING EXOGENOUS GLUCOAMYLASES, THE METHOD FOR OBTAINING SAID YEAST STRAINS AND THE USE THEREOF TO PRODUCE BIOETHANOL

(71) Applicant: LESAFFRE ET COMPAGNIE, Paris (FR)

(72) Inventors: Maud Petit, Marcq en Baroeul (FR); Georges Pignede, Marcq en Baroeul (FR); Jean-Michel Bavouzet, Croix (FR); Benoît Thomas, Marcq en Baroeul (FR)

(73) Assignee: LESAFFRE ET COMPAGNIE, Paris (FR)

( * ) Notice: Subject to any disclaimer, the term of this patent is extended or adjusted under 35 U.S.C. 154(b) by 209 days.

(21) Appl. No.: 15/755,675

(22) PCT Filed: Aug. 23, 2016

(86) PCT No.: PCT/FR2016/052107
§ 371 (c)(1),
(2) Date: Dec. 10, 2018

(87) PCT Pub. No.: WO2017/037362
PCT Pub. Date: Mar. 9, 2017

(65) Prior Publication Data
US 2019/0292532 A1    Sep. 26, 2019

(30) Foreign Application Priority Data
Aug. 31, 2015 (FR) ..................... 15 58079

(51) Int. Cl.
*C12N 9/34* (2006.01)
*C12N 15/81* (2006.01)
*C12P 7/06* (2006.01)

(52) U.S. Cl.
CPC ........... *C12N 9/2428* (2013.01); *C12N 15/81* (2013.01); *C12P 7/06* (2013.01); *Y02E 50/10* (2013.01)

(58) Field of Classification Search
None
See application file for complete search history.

(56) References Cited

PUBLICATIONS

Hostinova E et al. Yeast glucoamylases: molecular-genetic and structural characterization. 2010. Biologia 65/4:559-568 (Year: 2010).*
GenBank P69327.1. Genbank. 2014 p. 1-10. (Year: 2014).*
GenBank P69328.1. Genbank. 2014 p. 1-11. (Year: 2014).*
International Search Report dated Nov. 15, 2016, which issued during prosecution of International Application No. PCT/FR2016/052107.
Favaro, et al. "Consolidated bioprocessing of starchy substrates into ethanol by industrial *Saccharomyces cerevisiae* strains secreting fungal amylases" Biotechnology and Bioengineering, Jul. 2015, 112(9)1751-1760.
Kim et al. "Construction of a direct starch-fermenting industrial strain of *Saccharomyces cerevisiae* producing glucoamylase, alpha-amylase and debranching enzyme" Biotechnology Letters, May 2010, 32(5):713-719.
Latorre-Garcia, et al. "Overexpression of the glucoamylase-encoding STA1 gene of *Saccharomyces cerevisiae* var. diastaticus in laboratory and industrial strains of *Saccharomyces*" World Journal of Microbiology and Biotechnology, Aug. 2008, 24(12):2957-2963.
Viktor, et al. "Raw starch conversion by *Saccharomyces cerevisiae* expressing Aspergillus tubingensis amylases" Biotechnology for Biofuels, Nov. 29, 2013, 6(1):167.

* cited by examiner

*Primary Examiner* — Paul J Holland
(74) *Attorney, Agent, or Firm* — Duane Morris LLP; Thomas J. Kowalski; Deborah L. Lu

(57) ABSTRACT

The present application relates to improved *Saccharomyces cerevisiae* yeast strains that co-express a gene encoding a glucoamylase of fungal origin and a gene encoding the glucoamylase of *Saccharomyces cerevisiae* var. *diastaticus*. The present invention also relates to a method for obtaining these yeast strains involving
   a) genetically modifying a *Saccharomyces cerevisiae* yeast to co-express a gene encoding a glucoamylase of fungal origin and a gene encoding the glucoamylase of *Saccharomyces cerevisiae* var. *diastaticus*;
   b) culturing and fermenting the strain obtained in step a) on a dextrin medium;
   c) selecting the strains having fermentation kinetics at least equal to or greater than those obtained with the strain deposited at the CNCM [French National Collection of Microorganism Cultures] under number I 4999 under the same conditions.

The yeast strains according to the invention are of particular interest in producing bioethanol.

10 Claims, 13 Drawing Sheets

Specification includes a Sequence Listing.

SEQUENCE LISTING

<160> NUMBER OF SEQ ID NOS: 22

<210> SEQ ID NO 1
<211> LENGTH: 1923
<212> TYPE: DNA
<213> ORGANISM: Aspergillus niger

<400> SEQUENCE: 1

```
atgtccttta gatcattgct tgcactgtct ggtttagttt gcactggact tgccaatgtc      60
atctctaaga gagcgacact agattcctgg ttaagtaacg aagccactgt tgcacgtaca     120
gccatactta acaacatagg tgccgatgga gcatgggtta gtggcgcaga ttcggggata     180
gtcgttgcca gtccatcgac tgataatcct gactactttt atacctggac ccgtgatagt     240
gggttggtgc tgaaaacatt ggtagacctt ttcagaaacg gtgatacgtc cttgctatca     300
accatagaga attacattag cgcacaagct attgtacaag gcatttccaa tccgagtggc     360
```

```
gatctaagtt caggcgctgg cttgggtgaa cccaagttca atgtcgatga aactgcatat    420
acgggatcat ggggtagacc acaaagagat ggtccagctc taagagcaac tgccatgatt    480
ggatttggcc aatggctttt ggataatggc tacactagta cagccacaga cattgtttgg    540
cctttagtca gaaatgacct atcttatgtg gctcaatatt ggaaccaaac aggttatgac    600
ttatgggaag aagtcaatgg ttcttctttc tttacaattg ccgtacagca tcgtgcactg    660
gtggaaggat cggctttcgc cactgccgta ggttcctcat gtagttggtg tgattcacaa    720
gcgccagaga ttctatgcta tttgcagagc ttctggacag ggagttttat cttagccaac    780
ttcgatagct ctagatccgg gaaagatgct aatacccctat taggctcaat acacacgttt    840
gaccctgaag ctgcttgtga cgattctaca tttcaaccgt gttctcccag agctttggca    900
aaccataaaa aagttgttga ctctttttagg tctatctaca ccttaaacga cggtttgtcg    960
gattcagaag ctgtggcagt tgggaggtat ccggaggata cgtactacaa tggtaatcct   1020
tggttccttt gcactttggc agccgcggag cagttatatg atgcgttata tcaatgggat   1080
aagcagggtt ccttagaggt aactgatgtg tcgctggact tctttaaagc gctgtattca   1140
gatgctgcta ccggtacgta ttcttcgtca tcttcaacct attccagcat tgtggatgct   1200
gtcaagactt ttgcagacgg atttgtcagt atagttgaga ctcatgcagc ttctaatggt   1260
tctatgtccg aacagtacga caaaagcgat ggtgaacaat tgtcagcaag agacttgacc   1320
tggtcttatg cagccttgtt aacagccaac aataggagaa atagcgttgt tccagctagt   1380
tggggagaaa catccgcgtc atcagttcca ggaacgtgtg ctgctacttc agctattggt   1440
acatattctt cagttacagt cacctcttgg ccttcgatag tagctactgg aggaactact   1500
acgaccgcta ctcctacagg tagcggttct gtgacttcca cctcaaagac aactgctact   1560
gctagcaaaa catctaccct tacttcgtcc acatcatgca ctaccccaac tgcagtcgca   1620
gttacgtttg atttgacagc tactacaacg tacggggaaa acatttactt ggtaggtagc   1680
atcagtcaat gggcgactg ggaaaccagc gatggtattg cattgagtgc agataaatac   1740
acttcctctg atccattatg gtatgttacc gttacgttac cagctggtga gtccttttgaa   1800 tacaagttca tcagaatcga gagtgatgac tctgtggaat gggaatctga tcccaataga   1860
gaatacacag tacctcaagc gtgtggtaca tcaacagcca ccgtaactga tacttggagg   1920
taa                                                                  1923
```

<210> SEQ ID NO 2
<211> LENGTH: 640
<212> TYPE: PRT
<213> ORGANISM: Aspergillus niger

<400> SEQUENCE: 2

```
Met Ser Phe Arg Ser Leu Leu Ala Leu Ser Gly Leu Val Cys Thr Gly
1               5                   10                  15

Leu Ala Asn Val Ile Ser Lys Arg Ala Thr Leu Asp Ser Trp Leu Ser
            20                  25                  30

Asn Glu Ala Thr Val Ala Arg Thr Ala Ile Leu Asn Asn Ile Gly Ala
        35                  40                  45

Asp Gly Ala Trp Val Ser Gly Ala Asp Ser Gly Ile Val Val Ala Ser
    50                  55                  60

Pro Ser Thr Asp Asn Pro Asp Tyr Phe Tyr Thr Trp Thr Arg Asp Ser
65                  70                  75                  80

Gly Leu Val Leu Lys Thr Leu Val Asp Leu Phe Arg Asn Gly Asp Thr
```

```
            85                  90                  95
Ser Leu Leu Ser Thr Ile Glu Asn Tyr Ile Ser Ala Gln Ala Ile Val
            100                 105                 110

Gln Gly Ile Ser Asn Pro Ser Gly Asp Leu Ser Ser Gly Ala Gly Leu
            115                 120                 125

Gly Glu Pro Lys Phe Asn Val Asp Glu Thr Ala Tyr Thr Gly Ser Trp
            130                 135                 140

Gly Arg Pro Gln Arg Asp Gly Pro Ala Leu Arg Ala Thr Ala Met Ile
145                 150                 155                 160

Gly Phe Gly Gln Trp Leu Leu Asp Asn Gly Tyr Thr Ser Thr Ala Thr
                165                 170                 175

Asp Ile Val Trp Pro Leu Val Arg Asn Asp Leu Ser Tyr Val Ala Gln
                180                 185                 190

Tyr Trp Asn Gln Thr Gly Tyr Asp Leu Trp Glu Glu Val Asn Gly Ser
                195                 200                 205

Ser Phe Phe Thr Ile Ala Val Gln His Arg Ala Leu Val Glu Gly Ser
            210                 215                 220

Ala Phe Ala Thr Ala Val Gly Ser Ser Cys Ser Trp Cys Asp Ser Gln
225                 230                 235                 240

Ala Pro Glu Ile Leu Cys Tyr Leu Gln Ser Phe Trp Thr Gly Ser Phe
                245                 250                 255

Ile Leu Ala Asn Phe Asp Ser Ser Arg Ser Gly Lys Asp Ala Asn Thr
                260                 265                 270

Leu Leu Gly Ser Ile His Thr Phe Asp Pro Glu Ala Ala Cys Asp Asp
                275                 280                 285

Ser Thr Phe Gln Pro Cys Ser Pro Arg Ala Leu Ala Asn His Lys Glu
            290                 295                 300

Val Val Asp Ser Phe Arg Ser Ile Tyr Thr Leu Asn Asp Gly Leu Ser
305                 310                 315                 320

Asp Ser Glu Ala Val Ala Val Gly Arg Tyr Pro Glu Asp Thr Tyr Tyr
                325                 330                 335

Asn Gly Asn Pro Trp Phe Leu Cys Thr Leu Ala Ala Ala Glu Gln Leu
                340                 345                 350

Tyr Asp Ala Leu Tyr Gln Trp Asp Lys Gln Gly Ser Leu Glu Val Thr
                355                 360                 365

Asp Val Ser Leu Asp Phe Phe Lys Ala Leu Tyr Ser Asp Ala Ala Thr
                370                 375                 380

Gly Thr Tyr Ser Ser Ser Ser Thr Tyr Ser Ser Ile Val Asp Ala
385                 390                 395                 400

Val Lys Thr Phe Ala Asp Gly Phe Val Ser Ile Val Glu Thr His Ala
                405                 410                 415

Ala Ser Asn Gly Ser Met Ser Glu Gln Tyr Asp Lys Ser Asp Gly Glu
                420                 425                 430

Gln Leu Ser Ala Arg Asp Leu Thr Trp Ser Tyr Ala Ala Leu Leu Thr
            435                 440                 445

Ala Asn Asn Arg Arg Asn Ser Val Pro Ala Ser Trp Gly Glu Thr
450                 455                 460

Ser Ala Ser Ser Val Pro Gly Thr Cys Ala Ala Thr Ser Ala Ile Gly
465                 470                 475                 480

Thr Tyr Ser Ser Val Thr Val Thr Ser Trp Pro Ser Ile Val Ala Thr
                485                 490                 495

Gly Gly Thr Thr Thr Thr Ala Thr Pro Thr Gly Ser Gly Ser Val Thr
            500                 505                 510
```

```
Ser Thr Ser Lys Thr Thr Ala Thr Ala Ser Lys Thr Ser Thr Ser Thr
        515                 520                 525

Ser Ser Thr Ser Cys Thr Thr Pro Thr Ala Val Ala Val Thr Phe Asp
    530                 535                 540

Leu Thr Ala Thr Thr Thr Tyr Gly Glu Asn Ile Tyr Leu Val Gly Ser
545                 550                 555                 560

Ile Ser Gln Leu Gly Asp Trp Glu Thr Ser Asp Gly Ile Ala Leu Ser
                565                 570                 575

Ala Asp Lys Tyr Thr Ser Ser Asp Pro Leu Trp Tyr Val Thr Val Thr
            580                 585                 590

Leu Pro Ala Gly Glu Ser Phe Glu Tyr Lys Phe Ile Arg Ile Glu Ser
        595                 600                 605

Asp Asp Ser Val Glu Trp Glu Ser Asp Pro Asn Arg Glu Tyr Thr Val
    610                 615                 620

Pro Gln Ala Cys Gly Thr Ser Thr Ala Thr Val Thr Asp Thr Trp Arg
625                 630                 635                 640

<210> SEQ ID NO 3
<211> LENGTH: 2418
<212> TYPE: DNA
<213> ORGANISM: Saccharomyces cerevisiae var. diastaticus

<400> SEQUENCE: 3
atgcaaagac catttctact cgcttatttg gtcctttcgc ttctatttaa ctcagctttg      60
ggttttccaa ctgcactagt tcctagagga tcctcctcta gcaacatcac ttcctccggt     120
ccatcttcaa ctccattcag ctctgctact gaaagctttt ctactggcac tactgtcact     180
ccatcatcat ccaaataccc tggcagtaaa acagaaactt ctgtttcttc tacaaccgaa     240
actaccattg ttccaactac aactcgact tctgtcataa caccatcaac aaccactatt      300
accactacgg tttgctctac aggaacaaac tctgccggtg aaactacttc tggatgctct     360
ccaaagacca ttacaactac tgttccatgt caaccagtc caagcgaaac cgcatcggaa      420
tcaacaacca cttcacctac cacacctgta actacagttg tctcaaccac cgtcgttact     480
actgagtatt ctactagtac aaaacaaggt ggtgaaatta caactacatt tgtcaccaaa    540
aacattccaa ccacttacct aactacaatt gctccaactt catcagtcac tacggttacc     600
aatttcaccc caaccactat tactactacg tttgctctaa caggaacaaa ctctgccggt     660
gaaactacct ctggatgctc tccaaagact gtcacaacaa ctgttccttg ttcaactggt     720
actggcgaat acactactga agctaccgcc cctgttacaa cagctgtcac aaccaccgtt     780
gttaccactg aatcctctac gggtactaac tccgctggta agacgacaac tagttacaca    840
acaaagtctg taccaaccac ctatgtattt gactttggca agggcattct cgatcaaagc     900
tgcggcggtg tattttcaaa caacggctct tcgcaagtgc agctgcggga tgtagtcttg    960
atgaatggga cagtggtata cgattcaaac ggcgcttggg acagtagtcc gctggaggag   1020
tggctccagc gacagaaaaa agtttccatc gaaagaatat ttgaaaatat tgggcccagc   1080
gccgtgtatc cgtctatttt gcctggggtc gtgattgcgt caccatcgca aacgcatcca   1140
gactacttct accaatggat aagggacagc gcgttgacga taaacagtat tgtctctcat   1200
tctgcggacc cggcaataga gacgttattg cagtacctga cgtttcatt ccacttgcaa    1260 agaaccaaca cacattgggg cgctggcatt ggttacacta cgatacagt ggctttggga    1320 gaccctaagt ggaacgtcga caacacggct ttcacggaac cttggggtcg tcctcaaaac   1380
```

-continued

```
gatggccctg ctcttcgaag cattgccatc ttaaaaatca tcgactacat caagcaatct    1440
ggcactgatc tggggccaa gtacccattc cagtccaccg cagatatctt tgatgatatt     1500
gtacgttggg acctgaggtt cattattgac cactggaatt cttccggatt tgatctatgg    1560
gaggaagtca atgcatgca tttctttact ttactggtac aactgtctgc agtggacagg     1620
tcgctgtcgt attttaacgc ctcagaacgg tcgtctccct ttgttgaaga attgcgtcag    1680
acacgccggg acatctccaa gttttttagtg gaccctgcga atgggtttat caacggcaag   1740
tacaattata ttgttgagac acccatgatt gccgacacat tgagatccgg actggacata   1800
tccactttat tagctgcgaa caccgtccac gatgcgccat ctgcttccca tcttccgttc   1860
gatatcaatg accctgccgt cctgaacacg ttgcaccatt tgatgttgca catgcgttcg   1920 atataccccca tcaacgatag ctccaaaaat gcaacgggta ttgccctggg ccggtatcct   1980
gaggacgtat atgatggata tggcgttggc gagggaaatc cctgggtcct ggccacgtgt   2040
gccgcttcaa caacgcttta tcagctcatt tacagacaca tctctgagca gcatgacttg    2100
gttgtcccaa tgaacaacga ttgttcgaac gcatttggga gcgagctggt attctccaac    2160
ctcacgactt tgggaaatga cgaaggctat ttgattttgg agttcaatac acctgccttc    2220
aatcaaacca tacaaaaaat cttccaacta gctgattcat tcttggtca agctgaaagc     2280 cacgtgggaa cagacgggga actaagtgaa caatttaaca atacacagg gtttatgcag     2340 ggtgcccaac accttacctg gtcctatact tcattctggg atgcctatca aataagacaa    2400
gaagttttac agagtttg                                                 2418
```

<210> SEQ ID NO 4
<211> LENGTH: 806
<212> TYPE: PRT
<213> ORGANISM: Saccharomyces cerevisiae var. diastaticus

<400> SEQUENCE: 4

```
Met Gln Arg Pro Phe Leu Leu Ala Tyr Leu Val Leu Ser Leu Leu Phe
1               5                   10                  15

Asn Ser Ala Leu Gly Phe Pro Thr Ala Leu Val Pro Arg Gly Ser Ser
            20                  25                  30

Ser Ser Asn Ile Thr Ser Ser Gly Pro Ser Thr Pro Phe Ser Ser
        35                  40                  45

Ala Thr Glu Ser Phe Ser Thr Gly Thr Thr Val Thr Pro Ser Ser Ser
    50                  55                  60

Lys Tyr Pro Gly Ser Lys Thr Glu Thr Val Ser Ser Thr Glu
65                  70                  75                  80

Thr Thr Ile Val Pro Thr Thr Thr Thr Ser Val Ile Thr Pro Ser
                85                  90                  95

Thr Thr Thr Ile Thr Thr Thr Val Cys Ser Thr Gly Thr Asn Ser Ala
            100                 105                 110

Gly Glu Thr Thr Ser Gly Cys Ser Pro Lys Thr Ile Thr Thr Val
        115                 120                 125

Pro Cys Ser Thr Ser Pro Ser Glu Thr Ala Ser Glu Ser Thr Thr Thr
    130                 135                 140

Ser Pro Thr Thr Pro Val Thr Val Val Ser Thr Val Val Thr
145                 150                 155                 160

Thr Glu Tyr Ser Thr Ser Thr Lys Gln Gly Gly Glu Ile Thr Thr Thr
                165                 170                 175

Phe Val Thr Lys Asn Ile Pro Thr Thr Tyr Leu Thr Thr Ile Ala Pro
            180                 185                 190
```

```
Thr Ser Ser Val Thr Thr Val Thr Asn Phe Thr Pro Thr Thr Ile Thr
            195                 200                 205

Thr Thr Val Cys Ser Thr Gly Thr Asn Ser Ala Gly Glu Thr Thr Ser
            210                 215                 220

Gly Cys Ser Pro Lys Thr Val Thr Thr Val Pro Cys Ser Thr Gly
225                 230                 235                 240

Thr Gly Glu Tyr Thr Thr Glu Ala Thr Ala Pro Val Thr Thr Ala Val
                245                 250                 255

Thr Thr Thr Val Val Thr Thr Glu Ser Ser Thr Gly Thr Asn Ser Ala
            260                 265                 270

Gly Lys Thr Thr Thr Ser Tyr Thr Thr Lys Ser Val Pro Thr Thr Tyr
            275                 280                 285

Val Phe Asp Phe Gly Lys Gly Ile Leu Asp Gln Ser Cys Gly Gly Val
            290                 295                 300

Phe Ser Asn Asn Gly Ser Ser Gln Val Gln Leu Arg Asp Val Val Leu
305                 310                 315                 320

Met Asn Gly Thr Val Val Tyr Asp Ser Asn Gly Ala Trp Asp Ser Ser
                325                 330                 335

Pro Leu Glu Glu Trp Leu Gln Arg Gln Lys Lys Val Ser Ile Glu Arg
            340                 345                 350

Ile Phe Glu Asn Ile Gly Pro Ser Ala Val Tyr Pro Ser Ile Leu Pro
            355                 360                 365

Gly Val Val Ile Ala Ser Pro Ser Gln Thr His Pro Asp Tyr Phe Tyr
            370                 375                 380

Gln Trp Ile Arg Asp Ser Ala Leu Thr Ile Asn Ser Ile Val Ser His
385                 390                 395                 400

Ser Ala Asp Pro Ala Ile Glu Thr Leu Leu Gln Tyr Leu Asn Val Ser
                405                 410                 415

Phe His Leu Gln Arg Thr Asn Asn Thr Leu Gly Ala Gly Ile Gly Tyr
            420                 425                 430

Thr Asn Asp Thr Val Ala Leu Gly Asp Pro Lys Trp Asn Val Asp Asn
            435                 440                 445

Thr Ala Phe Thr Glu Pro Trp Gly Arg Pro Gln Asn Asp Gly Pro Ala
            450                 455                 460

Leu Arg Ser Ile Ala Ile Leu Lys Ile Ile Asp Tyr Ile Lys Gln Ser
465                 470                 475                 480

Gly Thr Asp Leu Gly Ala Lys Tyr Pro Phe Gln Ser Thr Ala Asp Ile
                485                 490                 495

Phe Asp Asp Ile Val Arg Trp Asp Leu Arg Phe Ile Ile Asp His Trp
            500                 505                 510

Asn Ser Ser Gly Phe Asp Leu Trp Glu Glu Val Asn Gly Met His Phe
            515                 520                 525

Phe Thr Leu Leu Val Gln Leu Ser Ala Val Asp Arg Ser Leu Ser Tyr
            530                 535                 540

Phe Asn Ala Ser Glu Arg Ser Ser Pro Phe Val Glu Glu Leu Arg Gln
545                 550                 555                 560

Thr Arg Arg Asp Ile Ser Lys Phe Leu Val Asp Pro Ala Asn Gly Phe
                565                 570                 575

Ile Asn Gly Lys Tyr Asn Tyr Ile Val Glu Thr Pro Met Ile Ala Asp
            580                 585                 590

Thr Leu Arg Ser Gly Leu Asp Ile Ser Thr Leu Leu Ala Ala Asn Thr
            595                 600                 605
```

```
Val His Asp Ala Pro Ser Ala Ser His Leu Pro Phe Asp Ile Asn Asp
    610                 615                 620
Pro Ala Val Leu Asn Thr Leu His His Leu Met Leu His Met Arg Ser
625                 630                 635                 640
Ile Tyr Pro Ile Asn Asp Ser Ser Lys Asn Ala Thr Gly Ile Ala Leu
                645                 650                 655
Gly Arg Tyr Pro Glu Asp Val Tyr Asp Gly Tyr Val Gly Glu Gly
                660                 665                 670
Asn Pro Trp Val Leu Ala Thr Cys Ala Ala Ser Thr Thr Leu Tyr Gln
            675                 680                 685
Leu Ile Tyr Arg His Ile Ser Glu Gln His Asp Leu Val Val Pro Met
    690                 695                 700
Asn Asn Asp Cys Ser Asn Ala Phe Trp Ser Glu Leu Val Phe Ser Asn
705                 710                 715                 720
Leu Thr Thr Leu Gly Asn Asp Glu Gly Tyr Leu Ile Leu Glu Phe Asn
                725                 730                 735
Thr Pro Ala Phe Asn Gln Thr Ile Gln Lys Ile Phe Gln Leu Ala Asp
            740                 745                 750
Ser Phe Leu Gly Gln Ala Glu Ser His Val Gly Thr Asp Gly Glu Leu
        755                 760                 765
Ser Glu Gln Phe Asn Lys Tyr Thr Gly Phe Met Gln Gly Ala Gln His
770                 775                 780
Leu Thr Trp Ser Tyr Thr Ser Phe Trp Asp Ala Tyr Gln Ile Arg Gln
785                 790                 795                 800
Glu Val Leu Gln Ser Leu
                805
```

```
<210> SEQ ID NO 5
<211> LENGTH: 71
<212> TYPE: DNA
<213> ORGANISM: Artificial Sequence
<220> FEATURE:
<223> OTHER INFORMATION: Amorce

<400> SEQUENCE: 5
tctgatggct aacggtgaaa ttaaagacat cgcaaacgtc acggctaact tgaagcttcg    60
tacgctgcag g                                                        71

<210> SEQ ID NO 6
<211> LENGTH: 52
<212> TYPE: DNA
<213> ORGANISM: Artificial Sequence
<220> FEATURE:
<223> OTHER INFORMATION: Amorce

<400> SEQUENCE: 6
tcactgtacg gtgagaacgt agatggtgtg cgcataggcc actagtggat ct            52

<210> SEQ ID NO 7
<211> LENGTH: 50
<212> TYPE: DNA
<213> ORGANISM: Artificial Sequence
<220> FEATURE:
<223> OTHER INFORMATION: Amorce

<400> SEQUENCE: 7
cacaccatct acgttctcac cgtacagtga gcataaccgc tagagtactt                50

<210> SEQ ID NO 8
```

```
<211> LENGTH: 50
<212> TYPE: DNA
<213> ORGANISM: Artificial Sequence
<220> FEATURE:
<223> OTHER INFORMATION: Amorce

<400> SEQUENCE: 8
ttacgtagac tgagtagcaa cggttgagga cagcttgcaa attaaagcct            50

<210> SEQ ID NO 9
<211> LENGTH: 50
<212> TYPE: DNA
<213> ORGANISM: Artificial Sequence
<220> FEATURE:
<223> OTHER INFORMATION: Amorce

<400> SEQUENCE: 9
tcctcaaccg ttgctactca gtctacgtaa gcataaccgc tagagtactt            50

<210> SEQ ID NO 10
<211> LENGTH: 50
<212> TYPE: DNA
<213> ORGANISM: Artificial Sequence
<220> FEATURE:
<223> OTHER INFORMATION: Amorce

<400> SEQUENCE: 10
tcagtagcac agagaagtgt aggagtgtag cagcttgcaa attaaagcct            50

<210> SEQ ID NO 11
<211> LENGTH: 50
<212> TYPE: DNA
<213> ORGANISM: Artificial Sequence
<220> FEATURE:
<223> OTHER INFORMATION: Amorce

<400> SEQUENCE: 11
ctacactcct acacttctct gtgctactga gcataaccgc tagagtactt            50

<210> SEQ ID NO 12
<211> LENGTH: 50
<212> TYPE: DNA
<213> ORGANISM: Artificial Sequence
<220> FEATURE:
<223> OTHER INFORMATION: Amorce

<400> SEQUENCE: 12
ttaggataca tgcagtagac gaggtaagca cagcttgcaa attaaagcct            50

<210> SEQ ID NO 13
<211> LENGTH: 50
<212> TYPE: DNA
<213> ORGANISM: Artificial Sequence
<220> FEATURE:
<223> OTHER INFORMATION: Amorce

<400> SEQUENCE: 13
tgcttacctc gtctactgca tgtatcctaa gcataaccgc tagagtactt            50

<210> SEQ ID NO 14
<211> LENGTH: 70
<212> TYPE: DNA
<213> ORGANISM: Artificial Sequence
<220> FEATURE:
<223> OTHER INFORMATION: Amorce

<400> SEQUENCE: 14
```

```
acatacttgc aatttataca gtgatgaccg ctgaatttgt atcttccata cagcttgcaa    60
attaaagcct                                                          70

<210> SEQ ID NO 15
<211> LENGTH: 70
<212> TYPE: DNA
<213> ORGANISM: Artificial Sequence
<220> FEATURE:
<223> OTHER INFORMATION: Amorce

<400> SEQUENCE: 15
taagggatat agaagcaaat agttgtcagt gcaatccttc aagacgattg gcataaccgc    60
tagagtactt                                                          70

<210> SEQ ID NO 16
<211> LENGTH: 70
<212> TYPE: DNA
<213> ORGANISM: Artificial Sequence
<220> FEATURE:
<223> OTHER INFORMATION: Amorce

<400> SEQUENCE: 16
cacatataca gcatcggaat gagggaaatt tgttcatatc gtcgttgagt cagcttgcaa    60
attaaagcct                                                          70

<210> SEQ ID NO 17
<211> LENGTH: 1545
<212> TYPE: DNA
<213> ORGANISM: Saccharomycopsis fibuligera

<400> SEQUENCE: 17
atgatcagat tgaccgttttt cttgaccgct gtttttgctg ctgttgcttc ttgtgttcca    60
gttgaattgg ataagagaaa caccggtcat ttccaagctt attctggtta taccgttgct   120
agatctaact tcacccaatg gattcatgaa caaccagctg tttcttggta ctacttgttg   180
caaaacatcg attacccaga aggtcaattc aaatctgcta accaggtgt tgttgttgct   240 tctccatcta catctgaacc agattacttc taccaatgga ctagagatac cgctattacc   300
ttcttgtcct tgattgctga agttgaagat cattctttct ccaacactac cttggctaag   360
gttgtcgaat attacatttc caacacctac accttgcaaa gagtttctaa tccatccggt   420
aacttcgatt ctccaaatca tgatggtttg ggtgaaccta agttcaacgt tgatgatact   480
gcttatacag cttcttgggg tagaccacaa aatgatggtc agctttgag agcttacgct   540 atttctagat acttgaacgc tgttgctaag cacaacaacg gtaaattatt attggccggt   600
caaaacggta ttcctattc ttctgcttcc gatatctact ggaagattat taagccagac   660
ttgcaacatg tttctactca ttggtctacc tctggttttg atttgtggga agaaaatcaa   720
ggtactcatt tcttcaccgc tttggttcaa ttgaaggctt tgtcttacgg tattccattg   780
tctaagacct acaatgatcc aggtttcact tcttggttgg aaaaacaaaa ggatgccttg   840
aactcctaca ttaactcttc cggtttcgtt aactctggta aaaagcacat cgttgaatct   900
ccacaattgt catctagagg tggttttgat tctgctactt atattgctgc cttgatcacc   960
catgatatcg gtgatgatga tacttacacc ccattcaatg ttgataactc ctacgttttg   1020
aactccttgt attacctatt ggtcgacaac aagaacagat acaagatcaa cggtaactac   1080
aaagctggtg ctgctgttgg tagatatcct gaagatgttt acaacggtgt tggtacttct   1140
```

```
gaaggtaatc catggcaatt ggctactgct tatgctggtc aaacttttta caccttggcc    1200
tacaattcct tgaagaacaa gaagaacttg gtcatcgaaa agttgaacta cgacttgtac    1260
aactccttca ttgctgattt gtccaagatt gattcttcct acgcttctaa ggattctttg    1320
actttgacct acggttccga taactacaag aacgttatca agtccttgtt gcaattcggt    1380
gactcattct tgaaggtttt gttggatcac atcgatgaca acggtcaatt gactgaagaa    1440
atcaacagat acaccggttt tcaagctggt gcagtttctt tgacttggtc atctggttct    1500
ttgttgtctg ctaatagagc cagaaacaag ttgatcgaat tattg                    1545
```

<210> SEQ ID NO 18
<211> LENGTH: 515
<212> TYPE: PRT
<213> ORGANISM: Saccharomycopsis fibuligera

<400> SEQUENCE: 18

```
Met Ile Arg Leu Thr Val Phe Leu Thr Ala Val Phe Ala Ala Val Ala
1               5                  10                 15

Ser Cys Val Pro Val Glu Leu Asp Lys Arg Asn Thr Gly His Phe Gln
            20                  25                  30

Ala Tyr Ser Gly Tyr Thr Val Ala Arg Ser Asn Phe Thr Gln Trp Ile
        35                  40                  45

His Glu Gln Pro Ala Val Ser Trp Tyr Tyr Leu Leu Gln Asn Ile Asp
    50                  55                  60

Tyr Pro Glu Gly Gln Phe Lys Ser Ala Lys Pro Gly Val Val Val Ala
65                  70                  75                  80

Ser Pro Ser Thr Ser Glu Pro Asp Tyr Phe Tyr Gln Trp Thr Arg Asp
                85                  90                  95

Thr Ala Ile Thr Phe Leu Ser Leu Ile Ala Glu Val Glu Asp His Ser
            100                 105                 110

Phe Ser Asn Thr Thr Leu Ala Lys Val Val Glu Tyr Tyr Ile Ser Asn
        115                 120                 125

Thr Tyr Thr Leu Gln Arg Val Ser Asn Pro Ser Gly Asn Phe Asp Ser
    130                 135                 140

Pro Asn His Asp Gly Leu Gly Glu Pro Lys Phe Asn Val Asp Asp Thr
145                 150                 155                 160

Ala Tyr Thr Ala Ser Trp Gly Arg Pro Gln Asn Asp Gly Pro Ala Leu
                165                 170                 175

Arg Ala Tyr Ala Ile Ser Arg Tyr Leu Asn Ala Val Ala Lys His Asn
            180                 185                 190

Asn Gly Lys Leu Leu Leu Ala Gly Gln Asn Gly Ile Pro Tyr Ser Ser
        195                 200                 205

Ala Ser Asp Ile Tyr Trp Lys Ile Ile Lys Pro Asp Leu Gln His Val
    210                 215                 220

Ser Thr His Trp Ser Thr Ser Gly Phe Asp Leu Trp Glu Glu Asn Gln
225                 230                 235                 240

Gly Thr His Phe Phe Thr Ala Leu Val Gln Leu Lys Ala Leu Ser Tyr
                245                 250                 255

Gly Ile Pro Leu Ser Lys Thr Tyr Asn Asp Pro Gly Phe Thr Ser Trp
            260                 265                 270

Leu Glu Lys Gln Lys Asp Ala Leu Asn Ser Tyr Ile Asn Ser Ser Gly
        275                 280                 285

Phe Val Asn Ser Gly Lys Lys His Ile Val Glu Ser Pro Gln Leu Ser
    290                 295                 300
```

```
Ser Arg Gly Gly Leu Asp Ser Ala Thr Tyr Ile Ala Ala Leu Ile Thr
305                 310                 315                 320

His Asp Ile Gly Asp Asp Thr Tyr Thr Pro Phe Asn Val Asp Asn
            325                 330                 335

Ser Tyr Val Leu Asn Ser Leu Tyr Tyr Leu Val Asp Asn Lys Asn
            340                 345                 350

Arg Tyr Lys Ile Asn Gly Asn Tyr Lys Ala Gly Ala Val Gly Arg
            355                 360                 365

Tyr Pro Glu Asp Val Tyr Asn Gly Val Gly Thr Ser Glu Gly Asn Pro
370                 375                 380

Trp Gln Leu Ala Thr Ala Tyr Ala Gly Gln Thr Phe Tyr Thr Leu Ala
385                 390                 395                 400

Tyr Asn Ser Leu Lys Asn Lys Lys Asn Leu Val Ile Glu Lys Leu Asn
            405                 410                 415

Tyr Asp Leu Tyr Asn Ser Phe Ile Ala Asp Leu Ser Lys Ile Asp Ser
            420                 425                 430

Ser Tyr Ala Ser Lys Asp Ser Leu Thr Leu Thr Tyr Gly Ser Asp Asn
            435                 440                 445

Tyr Lys Asn Val Ile Lys Ser Leu Leu Gln Phe Gly Asp Ser Phe Leu
450                 455                 460

Lys Val Leu Leu Asp His Ile Asp Asp Asn Gly Gln Leu Thr Glu Glu
465                 470                 475                 480

Ile Asn Arg Tyr Thr Gly Phe Gln Ala Gly Ala Val Ser Leu Thr Trp
            485                 490                 495

Ser Ser Gly Ser Leu Leu Ser Ala Asn Arg Ala Arg Asn Lys Leu Ile
            500                 505                 510

Glu Leu Leu
        515

<210> SEQ ID NO 19
<211> LENGTH: 70
<212> TYPE: DNA
<213> ORGANISM: Artificial Sequence
<220> FEATURE:
<223> OTHER INFORMATION: Amorce

<400> SEQUENCE: 19
cgctccagaa ttagcggacc tcttgagcgg tgagcctctg gcaaagaaga gcataaccgc    60
tagagtactt                                                          70

<210> SEQ ID NO 20
<211> LENGTH: 71
<212> TYPE: DNA
<213> ORGANISM: Artificial Sequence
<220> FEATURE:
<223> OTHER INFORMATION: Amorce

<400> SEQUENCE: 20
cgctccagaa ttagcggacc tcttgagcgg tgagcctctg gcaaagaaga tgaagcttcg    60
tacgctgcag g                                                        71

<210> SEQ ID NO 21
<211> LENGTH: 50
<212> TYPE: DNA
<213> ORGANISM: Artificial Sequence
<220> FEATURE:
<223> OTHER INFORMATION: Amorce

<400> SEQUENCE: 21
```

```
tcactgtacg gtgagaacgt agatggtgtg cagcttgcaa attaaagcct        50

<210> SEQ ID NO 22
<211> LENGTH: 70
<212> TYPE: DNA
<213> ORGANISM: Artificial Sequence
<220> FEATURE:
<223> OTHER INFORMATION: Amorce

<400> SEQUENCE: 22
ctcaagaacg taggacgata actggttgga aagcgtaaac acggagtcaa cagcttgcaa    60
attaaagcct                                                            70
```

YEAST STRAINS CO-EXPRESSING EXOGENOUS GLUCOAMYLASES, THE METHOD FOR OBTAINING SAID YEAST STRAINS AND THE USE THEREOF TO PRODUCE BIOETHANOL

RELATED APPLICATIONS AND INCORPORATION BY REFERENCE

The present patent application is filed pursuant to 35 U.S.C. § 371 as a U.S. National Phase Application of International Patent Application No. PCT/FR2016/052107, which was filed on Aug. 23, 2016, claiming the benefit of priority to French patent application number FR 15 58079 filed on Aug. 31, 2015. The International Application was published as WO 2017/037362 on Mar. 9, 2017. The content of each of the aforementioned patent applications is incorporated herein by reference in its entirety.

SEQUENCE LISTING

The instant application contains a Sequence Listing which has been submitted electronically in ASCII format and is hereby incorporated by reference in its entirety. Said ASCII copy, created on Feb. 26, 2018, is named 44980002022_SL.txt and is 28,692 bytes in size.

TECHNICAL FIELD OF THE INVENTION

The present invention relates to *Saccharomyces cerevisiae* yeast strains genetically modified such that they co-express genes encoding glucoamylases of fungal origin and of *Saccharomyces cerevisiae* var. *diastaticus*. Such strains are of particular interest in the production of biofuel, in particular of bioethanol. The present invention also relates to a process for obtaining these yeasts and also to the use of these yeasts for producing bioethanol.

TECHNICAL BACKGROUND

The use of biomass for the production of bioethanol has attracted considerable interest over the past few years. Ethanol produced from agricultural residues, from industrial waste and from rapidly growing plants has in particular been proposed as a promising alternative fuel.

Currently, "first-generation" bioethanol is produced mainly from cane sugar and from starch-rich seeds in Brazil and in the United States, respectively, using *Saccharomyces cerevisiae* yeast strains which make it possible to ferment glucose to ethanol with a high alcoholic titer, productivity and yield.

The process which enables the conversion of starch to bioethanol requires a prehydrolysis and a liquefaction of the starch of the biomass, the conversion of the liquefied starch into fermentable sugars (by hydrolysis of the starch) and the fermentation of these sugars into ethanol. The last two steps are often carried out simultaneously.

The starch hydrolysis requires the action of enzymes termed amylolytic, but, unfortunately, the majority of *S. cerevisiae* yeasts are devoid of enzymes of this type. Currently, the production of ethanol from biomass composed of starch consequently requires the addition of exogenous enzymes in two steps: a first step of adding exogenous amylolytic enzymes so as to prehydrolyze and liquefy the starch contained in the biomass; and a second step in which other exogenous enzymes are used to hydrolyze the liquefied starch and an *S. cerevisiae* yeast strain is used to ferment the fermentable sugars released.

The use of exogenous enzymes causes an increase in costs and in lost time that is not insignificant, and it would therefore be very advantageous to obtain yeast strains which are both capable of hydrolyzing the liquefied starch and capable of efficiently fermenting the sugars resulting from the hydrolysis of the liquefied starch.

INVENTION

In this context, the inventors of the present invention have developed a genetically modified strain of *Saccharomyces cerevisiae*, said strain co-expressing several exogenous glucoamylase genes. In particular, the *Saccharomyces cerevisiae* strains according to the invention co-express both a gene encoding a glucoamylase of fungal origin and also a gene encoding the glucoamylase of *Saccharomyces cerevisiae* var. *diastaticus*. The inventors have demonstrated that these strains are capable of hydrolyzing the liquefied starch extracted from the biomass while at the same time succeeding in efficiently fermenting the sugars resulting from this hydrolysis. Indeed, the use of a yeast strain according to the present invention makes it possible to replace all or part of the amount of exogenous enzymes required during the conversion of the liquefied starch into bioethanol.

Thus, according to a first aspect, the present invention relates to a *Saccharomyces cerevisiae* yeast strain, characterized in that it co-expresses:
  a gene encoding a glucoamylase of fungal origin; and
  a gene encoding the glucoamylase of *Saccharomyces cerevisiae* var. *diastaticus*.

The inventors have also developed a method for obtaining *Saccharomyces cerevisiae* strains having the capacity both to hydrolyze the starch and to ferment the sugars resulting from this hydrolysis.

Thus, according to a second aspect, the present invention relates to a method for obtaining a yeast strain, said method comprising the following steps:
  a) genetically modifying a *Saccharomyces cerevisiae* yeast so as to make it express a gene encoding a glucoamylase of fungal origin and a gene encoding the glucoamylase of *Saccharomyces cerevisiae* var. *diastaticus*;
  b) culturing and fermenting the strain obtained in step a) on a dextrin medium;
  c) selecting the strains having fermentation kinetics at least equal to or greater than those obtained with the strain deposited, pursuant to the treaty of Budapest, on Jul. 9, 2015, at the CNCM [French National Collection of Microorganism Cultures] under number 1-4999 under the same conditions.

According to another aspect, the present invention relates to a process for producing bioethanol from a biomass, characterized in that it comprises the following steps:
  a) prehydrolyzing and liquefying the starch of the biomass;
  b) bringing the liquefied starch obtained in step a) into contact with a *Saccharomyces cerevisiae* yeast modified according to the invention;
  c) hydrolyzing and fermenting the liquefied starch by means of said yeast;
  d) extracting the ethanol produced in step c).

In addition, the present invention relates to the use of a *Saccharomyces cerevisiae* yeast strain modified according to the invention for the production of biofuel.

DETAILED DESCRIPTION OF THE INVENTION

In order to obtain a yeast strain that can hydrolyze the starch and ferment the sugars resulting from the hydrolysis of the starch, the inventors have genetically modified a *Saccharomyces cerevisiae* strain so as to make it co-express two genes encoding exogenous glucoamylases.

Thus, a first subject of the present invention is a *Saccharomyces cerevisiae* yeast strain, characterized in that it expresses:
  a gene encoding a glucoamylase of fungal origin; and
  a gene encoding the glucoamylase of *Saccharomyces cerevisiae* var. *diastaticus*.

In particular, a subject of the present invention is a *Saccharomyces cerevisiae* yeast strain, characterized in that it expresses:
  a gene encoding a glucoamylase of fungal origin; and
  a gene encoding the glucoamylase of *Saccharomyces cerevisiae* var. *diastaticus*,
in which the glucoamylase of *Saccharomyces cerevisiae* var. *diastaticus* has the protein sequence SEQ ID No.: 4.

Surprisingly, the inventors have discovered that the specific use of a glucoamylase gene of *Saccharomyces cerevisiae* var. *diastaticus* and of a glucoamylase gene of fungal origin makes it possible to obtain strains with excellent hydrolysis capacities.

These results are particularly surprising since the glucoamylase of *Saccharomyces cerevisiae* var. *diastaticus* is known to have a much less efficient yield than that obtained with glucoamylases of fungal origin, which makes it an enzyme that is used very little by enzyme producers. This premise is for example demonstrated in the international patent application published under the reference WO 2011/153516, which describes the screening of enzymes, including the glucoamylase of *Saccharomyces cerevisiae* var. *diastaticus* (GenBank ID: AAA35107.1). In this document, the glucoamylase of *Saccharomyces cerevisiae* var. *diastaticus* is not retained as being of interest for its enzymatic activity.

The expression "yeast strain" denotes a relatively homogeneous population of yeast cells. A yeast strain is obtained from a clone, a clone being a population of yeast cells that is obtained from a single yeast cell.

The term "gene encoding the glucoamylase" is intended to mean herein an amino acid sequence which, when it is expressed, will give a functional glucoamylase protein.

The term "glucoamylase" is intended to mean herein an enzyme capable of hydrolyzing the α-1,4 glycosidic bonds of the crude or soluble starch starting from the non-reducing end of amylose and of amylopectin. Amylases are also known as amyloglucosidases or γ-amylases (MEDLINE reference: EC 3.2.1.3). In addition to acting on the α-1,4 bonds, the glucoamylase enzyme can slowly hydrolyze the α-1,6 bonds of the amylopectin molecules, provided that the neighboring bond in the sequence is an α-1,4 bond.

A glucoamylase of fungal origin is chosen from commercial glucoamylases known for their good enzymatic activity and, in particular, the glucoamylase of fungal origin is selected from the group consisting of: a glucoamylase of *Aspergillus niger*, a glucoamylase of *Saccharomycopsis fibuligera*, a glucoamylase of *Trichoderma reesei*, a glucoamylase of *Rhizopus oryzae*, a glucoamylase of *Aspergillus oryzae* and a glucoamylase of *Thermomyces lanuginosis*.

These glucoamylases are known to those skilled in the art, and their sequences are available under the following GenBank references (www.ncbi.nlm.nih.gov/genbank): *Trichoderma reesei* (ETS06561), *Rhizopus oryzae* (BAA00033), *Aspergillus oryzae* (BAA00841), *Thermomyces lanuginosis* (ABQ23180).

According to one particular embodiment, the glucoamylase of fungal origin is a glucoamylase of *Aspergillus niger* or of *Saccharomycopsis fibuligera*.

The glucoamylase of *Saccharomycopsis fibuligera* is encoded by the GLU0111 gene which has the nucleic sequence corresponding to SEQ ID No.: 17 and, as protein sequence, has the sequence corresponding to SEQ ID No.: 18. The glucoamylase of *Aspergillus niger* is encoded by the GLAA gene which has the nucleic sequence corresponding to SEQ ID No.: 1 and, as protein sequence, has the sequence corresponding to SEQ ID No.: 2.

The glucoamylase of *Saccharomyces cerevisiae* var. *diastaticus* is encoded by the STA1 gene which has the nucleic sequence corresponding to SEQ ID No.: 3 and, as protein sequence, has the sequence corresponding to SEQ ID No.: 4.

Thus, in one particular embodiment, a subject of the present invention is a *Saccharomyces cerevisiae* yeast strain, characterized in that it contains the nucleic sequence SEQ ID No.: 1 and the nucleic sequence SEQ ID No.: 3.

In one embodiment, a subject of the present invention is a *Saccharomyces cerevisiae* yeast strain, characterized in that it co-expresses:
  a gene encoding the glucoamylase of *Aspergillus niger;* and
  a gene encoding the glucoamylase of *Saccharomyces cerevisiae* var. *diastaticus*.

In one particular embodiment, the invention relates to a *Saccharomyces cerevisiae* yeast strain, characterized in that it co-expresses:
  a gene encoding the glucoamylase of *Aspergillus niger;* and
  a gene encoding the glucoamylase of *Saccharomyces cerevisiae* var. *diastaticus*,
in which the glucoamylase of *Saccharomyces cerevisiae* var. *diastaticus* has the protein sequence SEQ ID No.: 4 and the glucoamylase of *Aspergillus niger* has the protein sequence SEQ ID No.: 2.

The expressions "glucoamylase of fungal origin" and "glucoamylase of *Saccharomyces cerevisiae* var. *diastaticus*" should not be interpreted strictly: they encompass glucoamylases of fungal origin and of *Saccharomyces cerevisiae* var. *diastaticus* which are encoded by the nucleic sequences as described above, but also the functional variants of these glucoamylases.

Typically, a functional variant of a glucoamylase according to the invention has a protein sequence having a percentage identity of at least 80%, 90%, 95%, more particularly of 99%, with the protein sequence of said glucoamylase. For example, the functional variants of the glucoamylases of *Aspergillus niger* and of *Saccharomyces cerevisiae* var. *diastaticus* have a protein sequence having a percentage identity of at least 80%, 90%, 95%, more particularly of 99%, respectively, with the sequence SEQ ID No.: 2 or 4.

The "percentage identity" is a comparison between amino acid sequences, and is determined by comparing two sequences that have been optimally aligned on a comparison window. Those skilled in the art know how to calculate a percentage identity between two sequences and have many tools enabling them to do so. One of the two sequences can have amino acid insertions, substitutions and deletions compared with the other sequence.

Those skilled in the art will know how to select functional variants of the glucoamylases according to the invention. The term "functional variant" is intended to mean a variant which retains its glucoamylase activity, this being with similar starch hydrolysis kinetics characteristics. Methods for measuring and comparing starch hydrolysis kinetics are described in the experimental section of the present application. Functional variants can be prepared by various conventional methods, such as for example random mutagenesis or site-directed mutagenesis.

Those skilled in the art are aware of many methods for introducing a gene into a yeast strain, in particular via the use of vectors comprising expression cassettes. The term "vector" is intended to mean any DNA sequence into which it is possible to insert foreign nucleic acid fragments, the vectors making it possible to introduce foreign DNA into a host cell. Examples of vectors are plasmids, cosmids, and virus-derived vectors. The vectors allow either the integration of the heterologous genes directly into the yeast genome, or the expression thereof in an independent plasmid.

The introduction of vectors into a host cell is a process widely known to those skilled in the art. Several methods are in particular described in "Current Protocols in Molecular Biology", 13.7.1-13.7.10; or else in Ellis T. et al., Integrative Biology, 2011, 3(2), 109-118.

According to the invention, the gene encoding a glucoamylase of fungal origin and the gene encoding the glucoamylase of *Saccharomyces cerevisiae* var. *diastaticus* can be inserted into one and the same vector, or into two separate vectors.

Thus, according to one particular aspect of the invention, the gene encoding a glucoamylase of fungal origin and the gene encoding the glucoamylase of *Saccharomyces cerevisiae* var. *diastaticus* are each integrated separately into a vector. According to one particular embodiment, the vector is a plasmid.

In one particular embodiment of the invention, the gene encoding a glucoamylase of fungal origin and the gene encoding the glucoamylase of *Saccharomyces cerevisiae* var. *diastaticus* are integrated into the genome of said yeast.

The vector according to the invention may also carry a selectable marker. The term "selectable marker" is intended to mean a gene of which the expression confers, on the yeasts which contain it, a characteristic which makes it possible to select them. It is for example an antibiotic-resistance gene or a gene which allows the yeast to grow on a particular medium.

The genes according to the invention can be functionally linked to a promoter, a terminator or any other sequence required for its expression in yeast.

In one particular mode of the invention, the expression of the genes encoding the glucoamylases of fungal origins and of *Saccharomyces cerevisiae* var. *diastaticus* is controlled by a "strong" promoter. Those skilled in the art know what "strong promoter" means. A strong promoter is for example the pADH1 promoter, the pTEF promoter or the pTDH3 promoter.

Thus, in one embodiment, the present invention relates to a *Saccharomyces cerevisiae* yeast strain as described above, in which the expression of the gene encoding a glucoamylase of fungal origin and the gene encoding the glucoamylase of *Saccharomyces cerevisiae* var. *diastaticus* is controlled by the pADH1 promoter.

The genes encoding the glucoamylases of fungal origins and of *Saccharomyces cerevisiae* var. *diastaticus* can be present as several copies.

Thus, in one particular embodiment, the present invention relates to a *Saccharomyces cerevisiae* yeast strain as described above, characterized in that it comprises m copies of the gene encoding a glucoamylase of fungal origin and n copies of the gene encoding the glucoamylase of *Saccharomyces cerevisiae* var. *diastaticus*, where m is an integer between 2 and 10 and n is an integer between 2 and 10.

m and n are therefore independently equal to 2, 3, 4, 5, 6, 7, 8, 9 or 10.

In one more particular embodiment, m is an integer between 2 and 8, and n is an integer between 2 and 8.

The invention relates particularly to the *Saccharomyces cerevisiae* yeast strains as described above, said strains being the strain deposited, pursuant to the treaty of Budapest, on Aug. 6, 2015, at the CNCM under number I-5005 or the strain deposited, pursuant to the treaty of Budapest, on Jul. 9, 2015, at the CNCM under number I-4997.

The I-5005 and I-4997 yeast strains comprise at least 4 copies of the gene encoding the glucoamylase of *Aspergillus niger* and at least 3 copies of the gene encoding the glucoamylase of *Saccharomyces cerevisiae* var. *diastaticus*.

The invention also relates to two *Saccharomyces cerevisiae* yeast strains as described above, said strains being the strain deposited, pursuant to the treaty of Budapest, on Aug. 11, 2016, at the CNCM under number I-5119 or the strain deposited, pursuant to the treaty of Budapest, on Aug. 11, 2016, at the CNCM under number I-5120.

The I-5119 yeast strain comprises 8 copies of the gene encoding the glucoamylase of *Aspergillus niger* and 4 copies of the gene encoding the glucoamylase of *Saccharomyces cerevisiae* var. *diastaticus*.

The I-5120 yeast strain comprises 4 copies of the gene encoding the glucoamylase of *Aspergillus niger* and 8 copies of the gene encoding the glucoamylase of *Saccharomyces cerevisiae* var. *diastaticus*.

The invention also relates to two *Saccharomyces cerevisiae* yeast strains as described above, said strains being the strain deposited, pursuant to the treaty of Budapest, on Aug. 11, 2016, at the CNCM under number I-5121 or the strain deposited, pursuant to the treaty of Budapest, on Aug. 11, 2016, at the CNCM under number I-5122.

The I-5121 yeast strain comprises 4 copies of the gene encoding the glucoamylase of *Saccharomycopsis fibuligera* and 4 copies of the gene encoding the glucoamylase of *Saccharomyces cerevisiae* var. *diastaticus*.

The I-5122 yeast strain comprises 4 copies of the gene encoding the glucoamylase of *Saccharomycopsis fibuligera* and 8 copies of the gene encoding the glucoamylase of *Saccharomyces cerevisiae* var. *diastaticus*.

The inventors have, in parallel, developed a method for obtaining *Saccharomyces cerevisiae* strains which are capable of hydrolyzing starch.

Thus, according to another aspect, a subject of the present invention is a method for obtaining a yeast strain, said method comprising the following steps:

a) genetically modifying a *Saccharomyces cerevisiae* yeast so as to make it co-express a gene encoding a glucoamylase of fungal origin and a gene encoding the glucoamylase of *Saccharomyces cerevisiae* var. *diastaticus*;

b) culturing and fermenting the strain obtained in step a) on a dextrin medium;

c) selecting the strains having fermentation kinetics at least equal to or greater than those obtained with the reference strain deposited, pursuant to the treaty of Budapest, on Jul. 9, 2015, at the CNCM under number I-4999 under the same conditions.

The *Saccharomyces cerevisiae* yeast of step a) is a yeast used for the production of bioethanol.

According to one particular embodiment of the invention, the *Saccharomyces cerevisiae* yeast of step a) is the Ethanol Red® yeast, hereinafter referred to as ER, deposited, on Sep. 4, 2008, at the CNCM under number I-4071.

The term "dextrin medium" is intended to mean a synthetic medium containing dextrins as known to those skilled in the art. It is, for example, a synthetic medium containing starch dextrins (220 g/kg), yeast extract (5 g/kg), urea (2 g/kg), potassium dihydrogen phosphate (1 g/kg) and also minerals and vitamins.

The I-4999 reference strain corresponds to the genetically modified Ethanol Red® yeast strain comprising 4 copies of the gene encoding the glucoamylase of *Saccharomycopsis fibuligera*.

The fermentation kinetics can be easily measured by various techniques known to those skilled in the art. For example, the fermentation kinetics can be measured via fermentation monitoring by weighing over time.

The strains thus selected are particularly advantageous for producing biofuel, in particular bioethanol, from biomass.

The term "biomass" denotes a collection of organic matter which can be converted into energy. Numerous types of biomass, including wood, agricultural residues, herbaceous crops, can be used for the production of biofuel, particularly of bioethanol. Bioethanol is characterized as "bio" because it is produced from renewable biomass.

Thus, the present invention relates to a process for producing bioethanol from a biomass, characterized in that it comprises the following steps:

a) prehydrolyzing and liquefying the starch of the biomass;
b) bringing the liquefied starch obtained in step a) into contact with a yeast according to the invention;
c) hydrolyzing and fermenting the liquefied starch by means of said yeast;
d) extracting the ethanol produced in step c).

According to one particular embodiment, the process for producing bioethanol described above also comprises a step b') of adding exogenous glucoamylase enzymes after step b) and/or during step c).

The ethanol thus produced can have many uses, in particular in the motor vehicle industry.

The invention also relates to the use of a yeast strain as described above, for the production of biofuel, in particular of bioethanol.

BRIEF DESCRIPTION OF THE FIGURES

DEPOSITS

The Deposits with INSTITUT PASTEUR COLLECTION NATIONALE DE CULTURES DE MICROORGANISMES (CNCM), under deposit accession numbers I-5005, deposited Aug. 6, 2015, I-4997, deposited Jul. 9, 2015, I-5119, deposited Aug. 11, 2016, I-5120, deposited Aug. 11, 2016, I-5121, deposited Aug. 11, 2016, and I-5122, deposited Aug. 11, 2016, were made and accepted pursuant to the terms of the Budapest Treaty. Upon issuance of a patent, all restrictions upon the deposit will be removed, and the deposit is intended to meet the requirements of 37 CFR §§ 1.801-1.809. The deposit will be irrevocably and without restriction or condition released to the public upon the issuance of a patent and for the enforceable life of the patent. The deposit will be maintained in the depository for a period of 30 years, or 5 years after the last request, or for the effective life of the patent, whichever is longer, and will be replaced if necessary during that period.

Figure 1A:
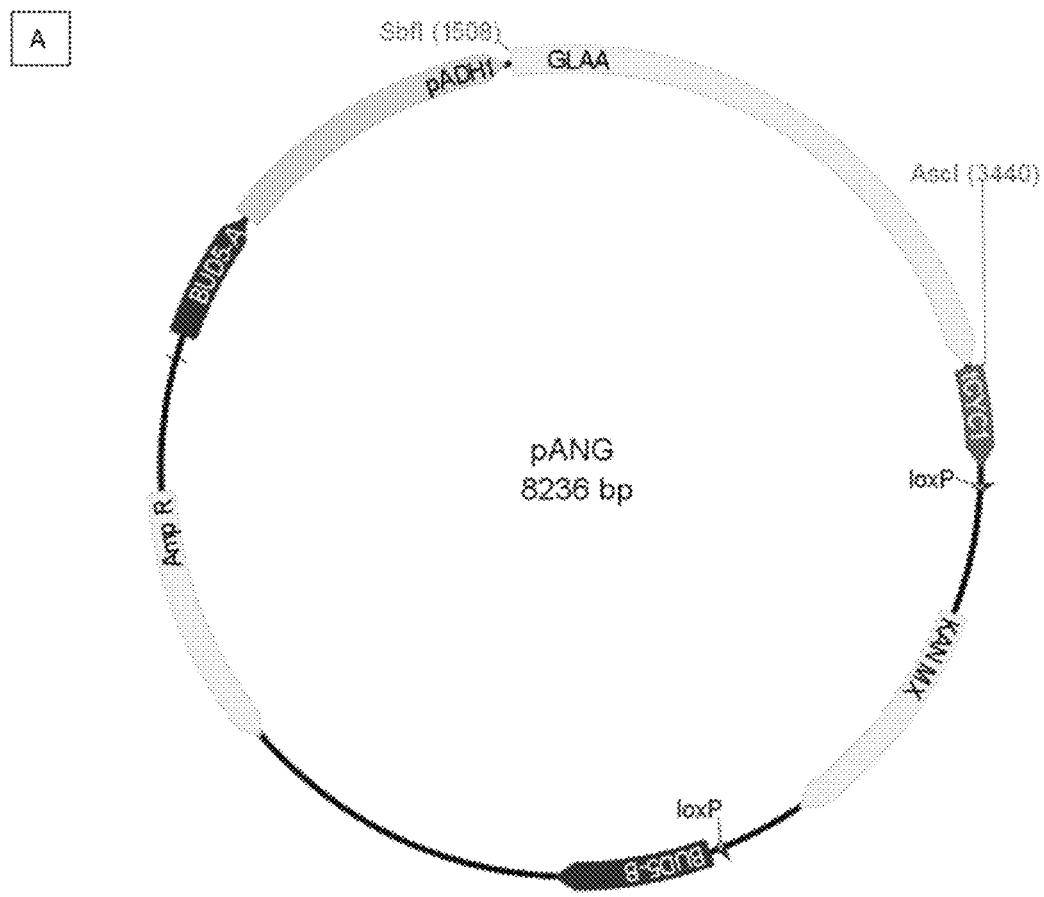
Figure 1B:
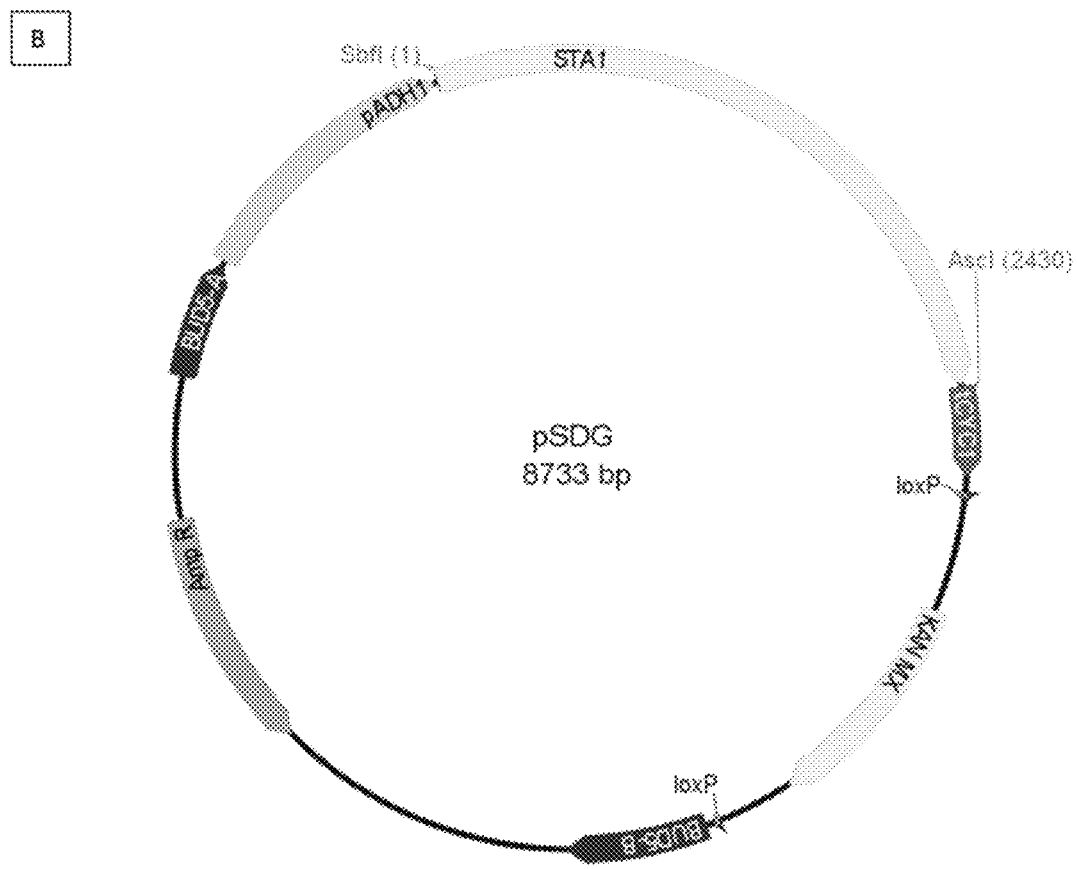

FIG. 1A-B shows two examples of overexpression and cloning vectors pANG and pSDG for the glucoamylases. This vector is an integrative cloning vector used for gene expression in yeast. pADH1: ADH1 promoter of *S. cerevisiae;* tCYC1: CYC1 terminator of *S. cerevisiae;* Kan-MX: geneticin-resistance marker; AmpR: ampicillin-resistance marker. BUD5-A and BUD5-B: the recombinogenic regions for the integration at the BUD5 locus.

Figure 2:
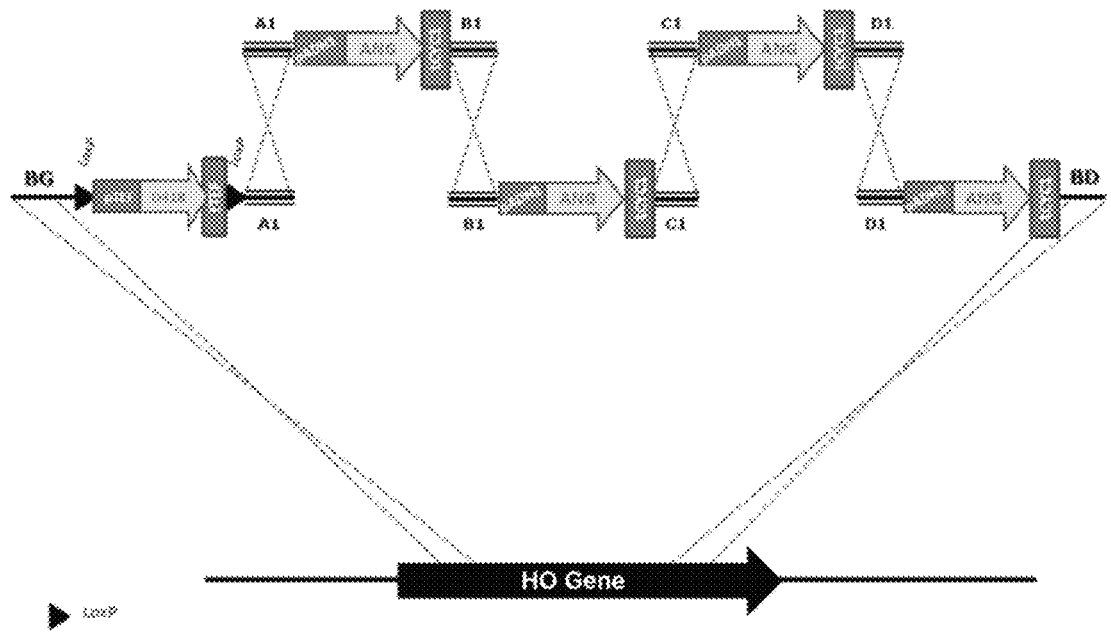

FIG. 2 describes the cloning strategy for the insertion of 4 expression modules and one selection module at the HO locus.

Figure 3:
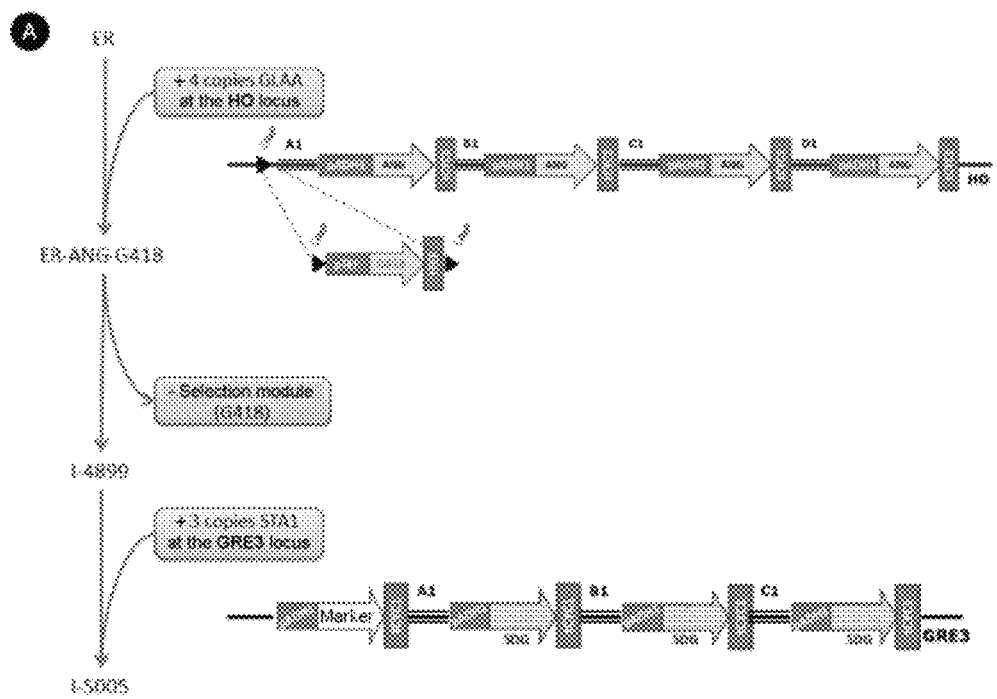

FIG. 3 describes the strategy and the various steps for obtaining the I-5005 strain (A).

Figure 4:
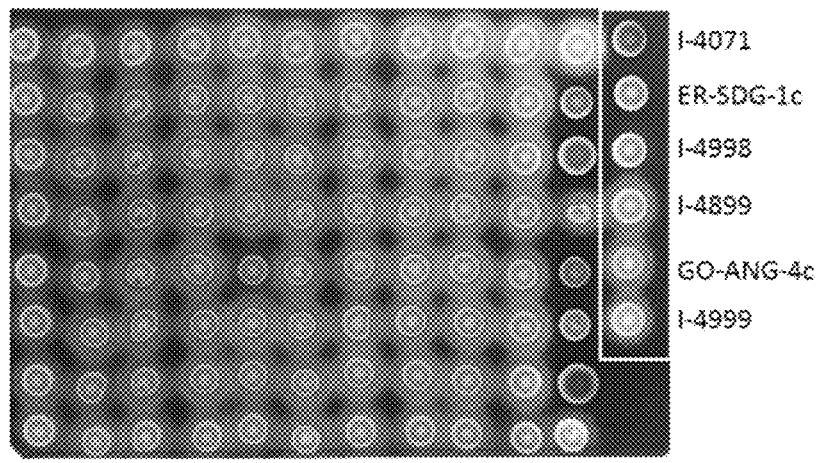

FIG. 4 shows an example of a result of screening 88 ER-GAND clones on a YEG/starch medium. After incubation for 48 h, the hydrolysis of the starch appears as clear halos around the yeast colonies secreting functional glucoamylases. The yeasts 1 to 6 on the 12th column are control strains which allow comparison of the size and intensity of the halos.

Figure 5:
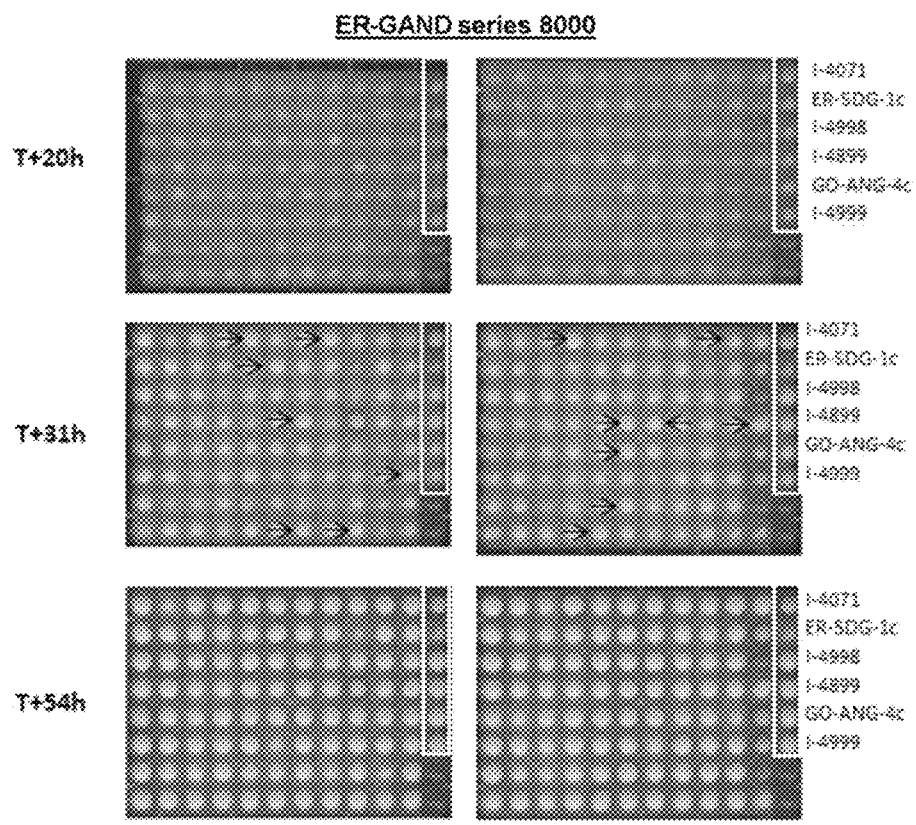

FIG. 5 shows the screening carried out with the ER-GAND series 8000 clones by fermentation on dextrin medium. Three fermentation times (20 h, 31 h and 54 h) are presented. The arrows indicate the 15 ER-GAND-series 8000 clones selected.

Figure 6:
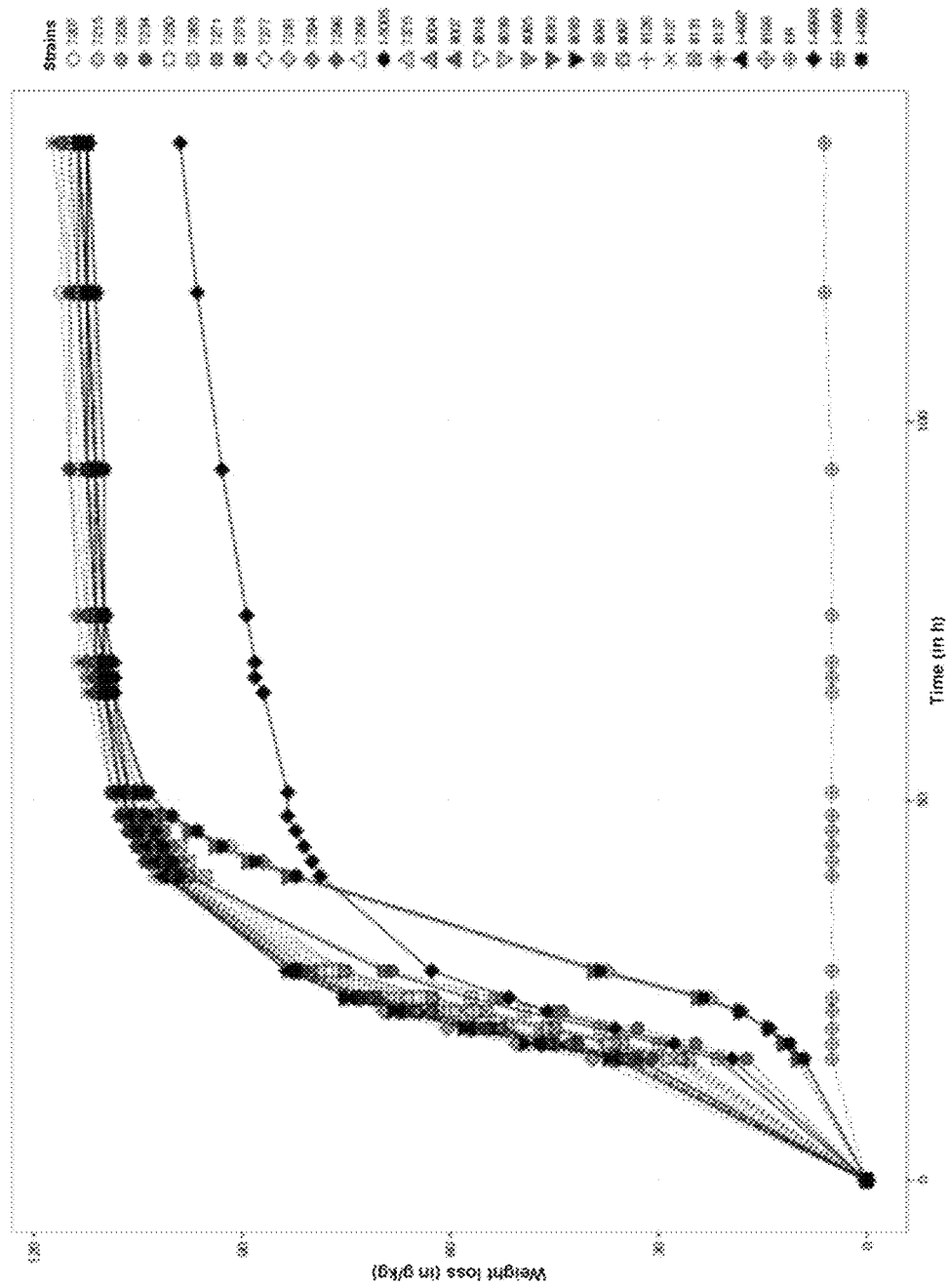

FIG. 6 represents a fermentation on dextrin medium of the best 30 ER-GAND clones screened and also of 4 control strains (ER, I-4998; I-4899 and I-4999). The fermentation is carried out at 32° C. and is monitored by weight loss (g/kg) for 74 h.

Figure 7:
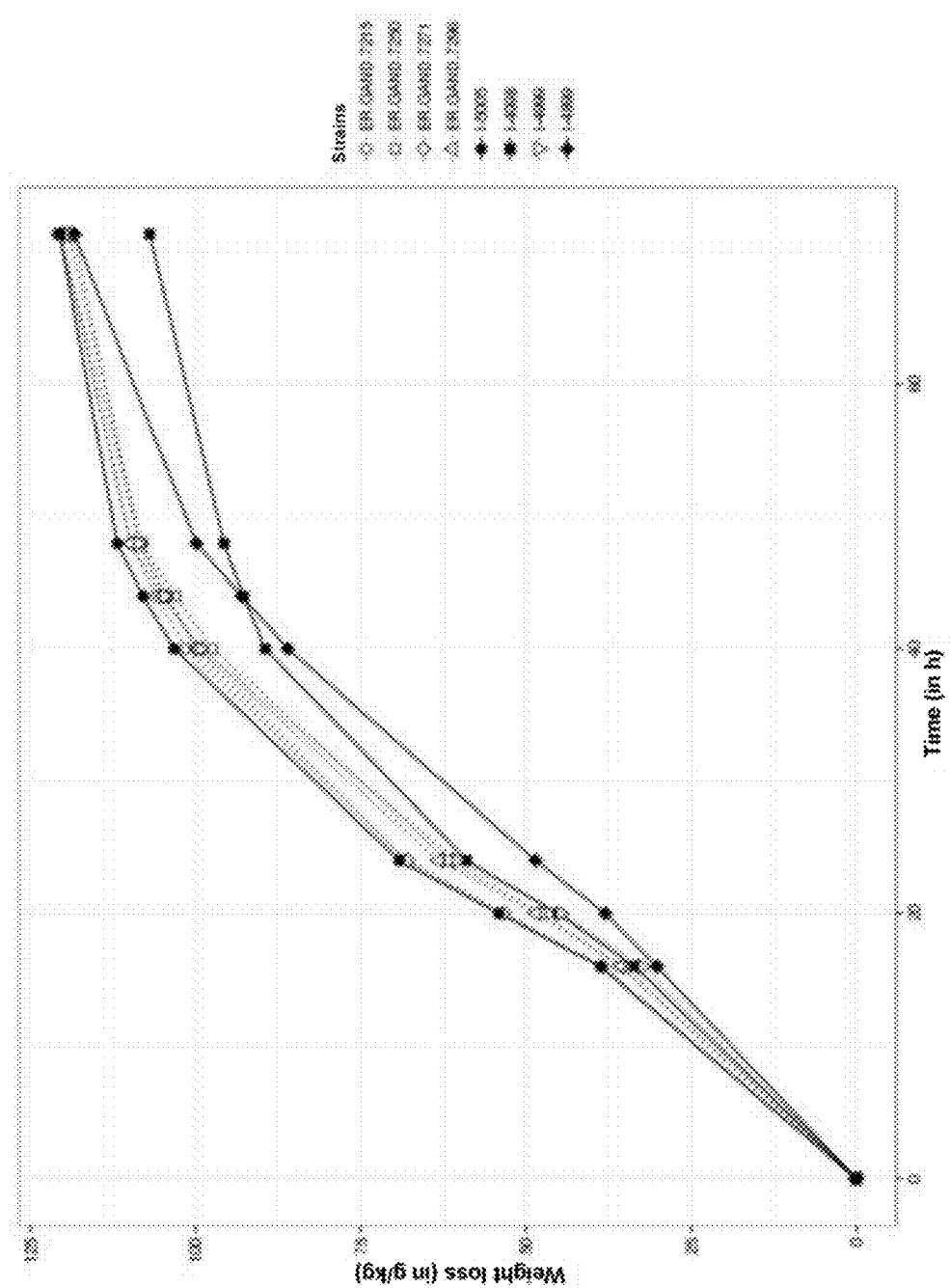

FIG. 7 represents a fermentation on industrial corn medium of the best 5 ER-GAND series 7000 clones screened and also of 3 control strains (I-4998; I-4899 and I-4999). The fermentation is carried out at 32° C. and is monitored by weight loss (g/kg) for 70 h.

Figure 8:
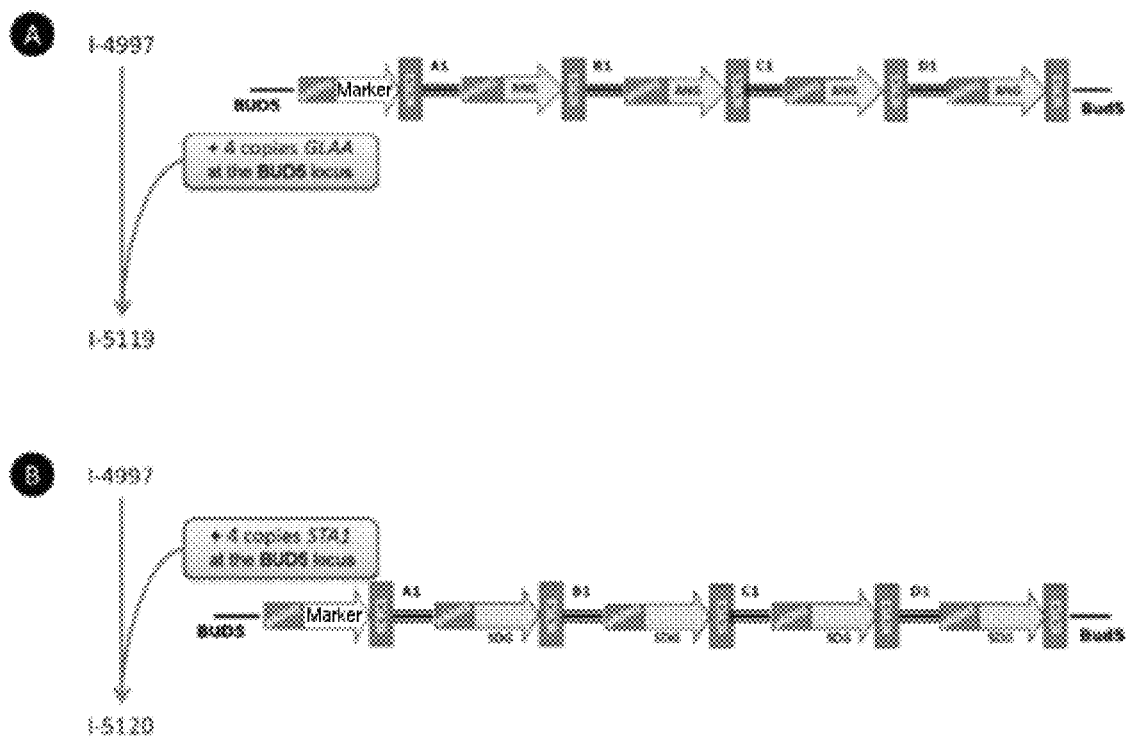

FIG. 8 describes the strategy and the various steps for obtaining the I-5119 (A) and I-5210 (B) strains.

Figure 9:
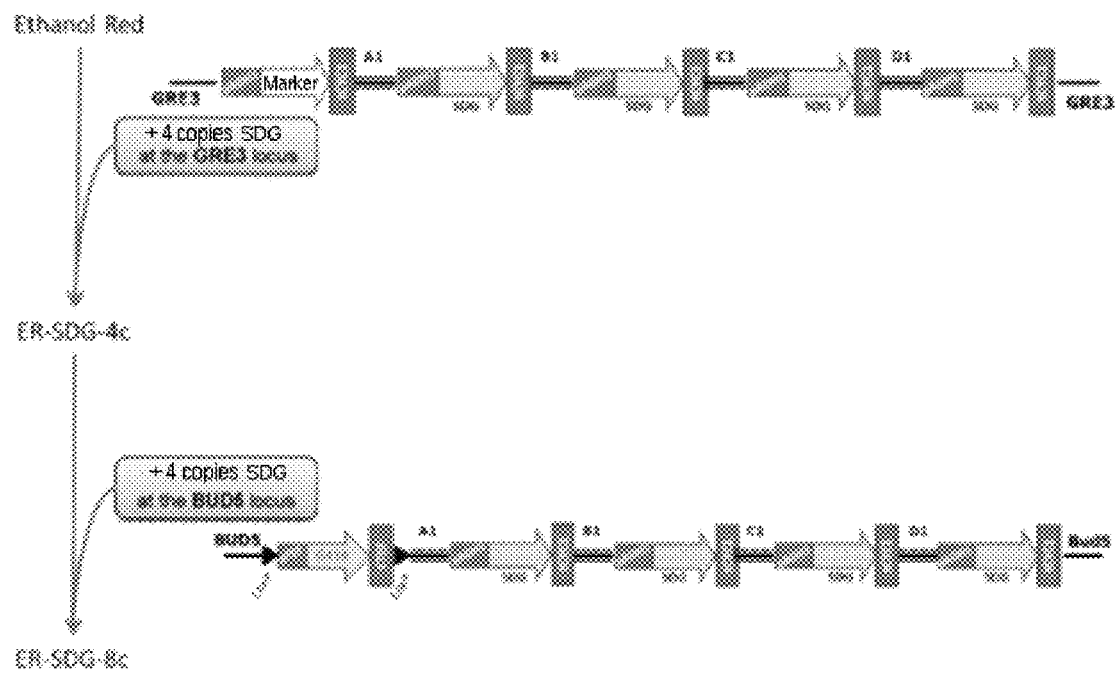

FIG. 9 describes the strategy and the various steps for obtaining the ER-SDG-4c and ER-SDG-8c control strains.

Figure 10:
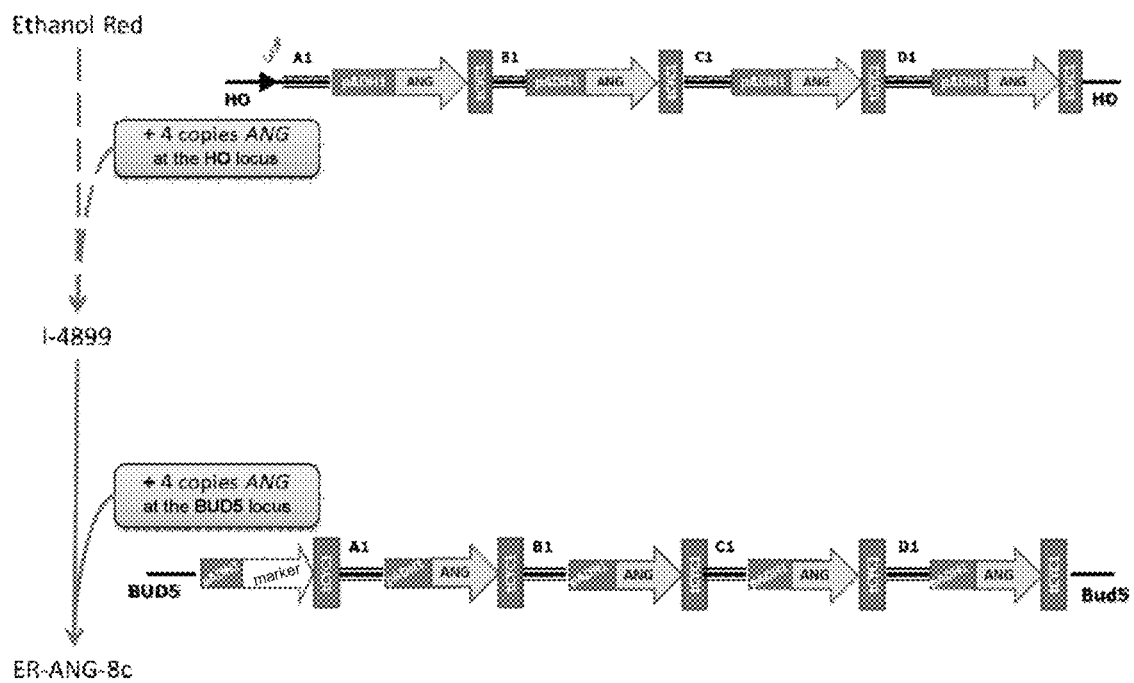

FIG. 10 describes the strategy and the various steps for obtaining the ER-ANG-8c strain.

Figure 11:
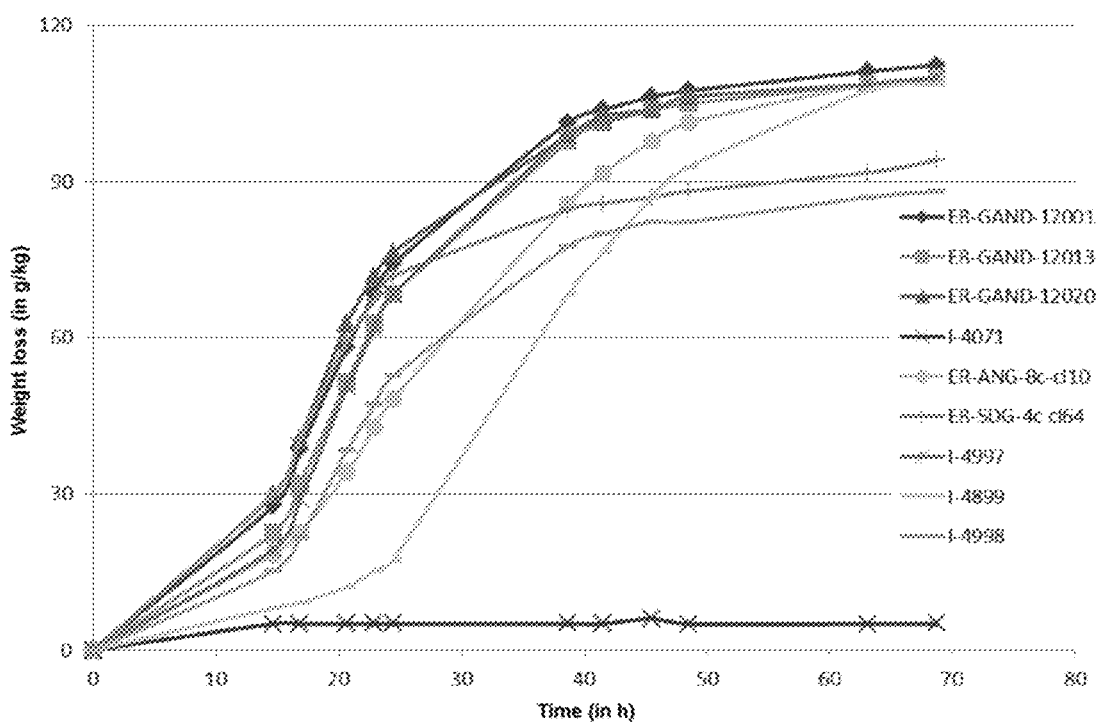

FIG. 11 represents a fermentation on dextrin medium of the best 3 ER-GAND-12000 clones screened and also of 6 control strains (I-4071, I-4899, I-4997, I-4998, ER-ANG-8c, and ER-SDG-4c). The fermentation is carried out at 32° C. and is monitored by weight loss (g/kg) for 70 h.

Figure 12:
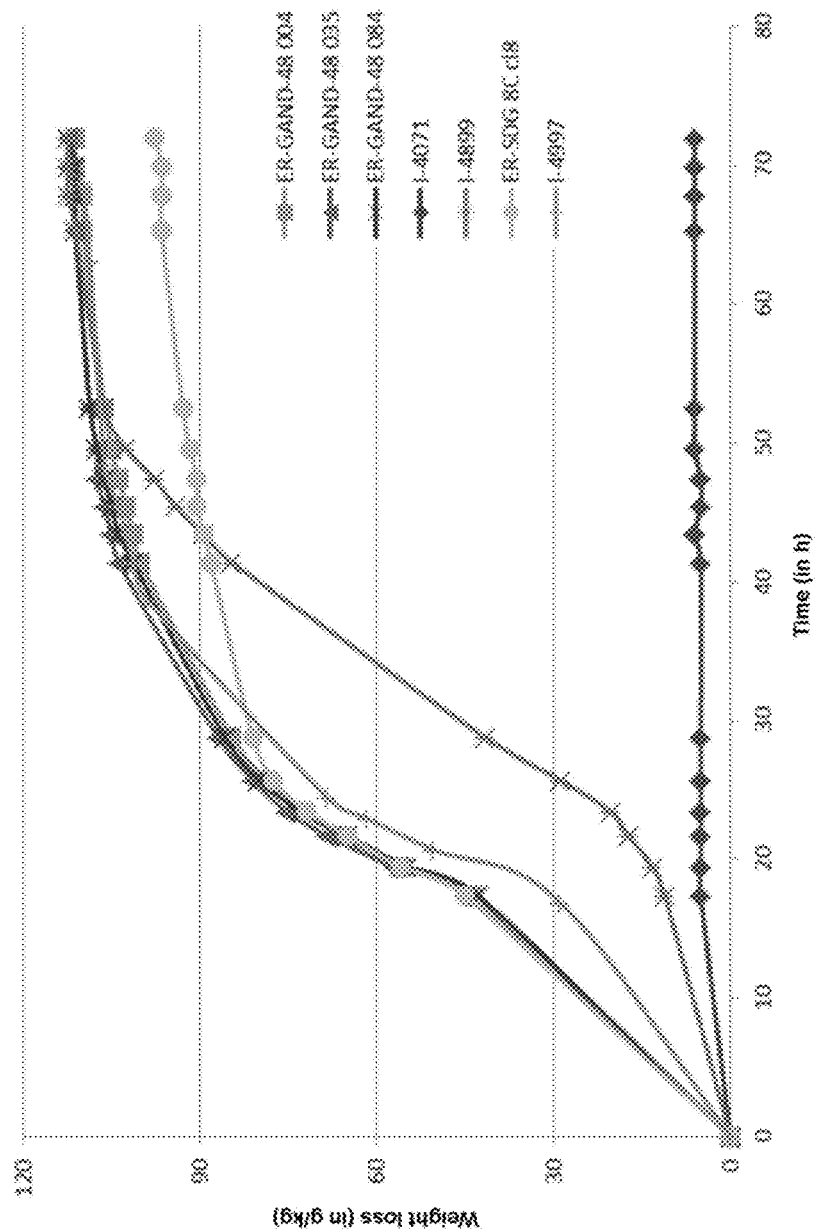

FIG. 12 represents a fermentation on dextrin medium of the best 3 ER-GAND-48000 clones screened and also of 4 control strains (I-4071, I-4899, I-4997 and ER-SDG-8c). The fermentation is carried out at 32° C. and is monitored by weight loss (g/kg) for 70 h.

Figure 13:
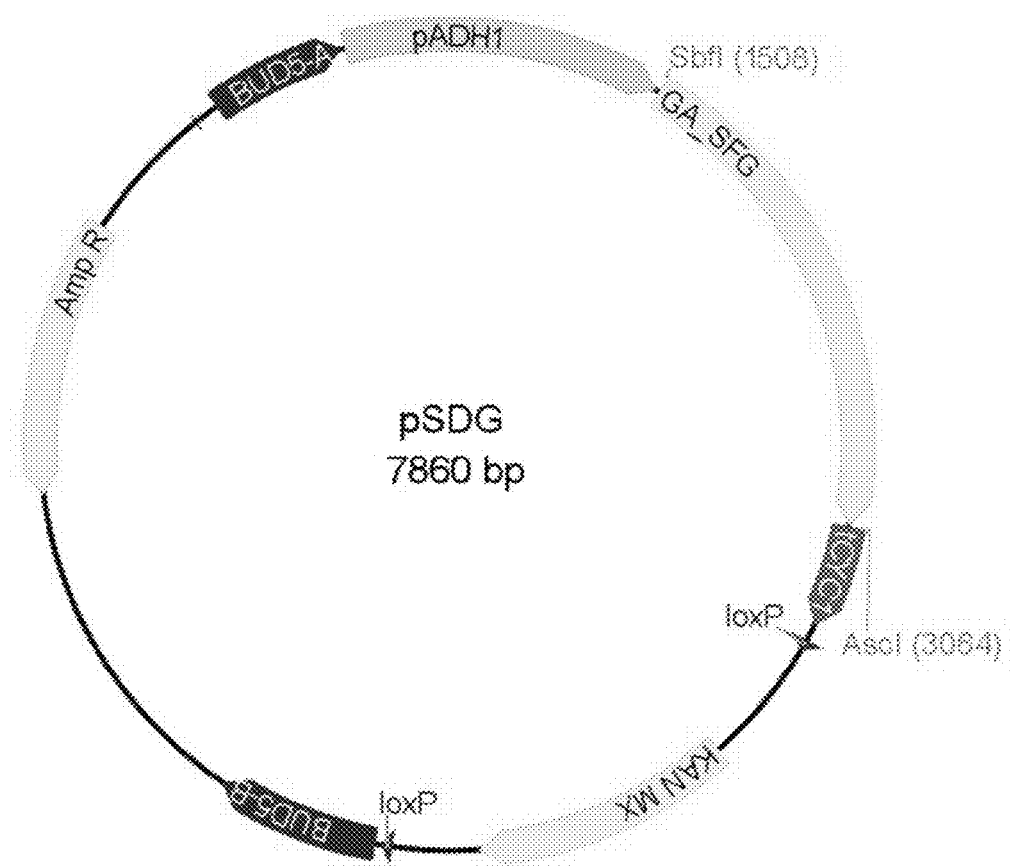

FIG. 13 represents an example of an overexpression and cloning vector pSFG for the glucoamylases. This vector is an integrative cloning vector used for gene expression in yeast. pADH1: ADH1 promoter of *S. cerevisiae;* tCYC1: CYC1 terminator of *S. cerevisiae;* Kan-MX: geneticin-resistance marker; AmpR: ampicillin-resistance marker. BUD5-A and BUD5-B: the recombinogenic regions for the integration at the BUD5 locus.

Figure 14:
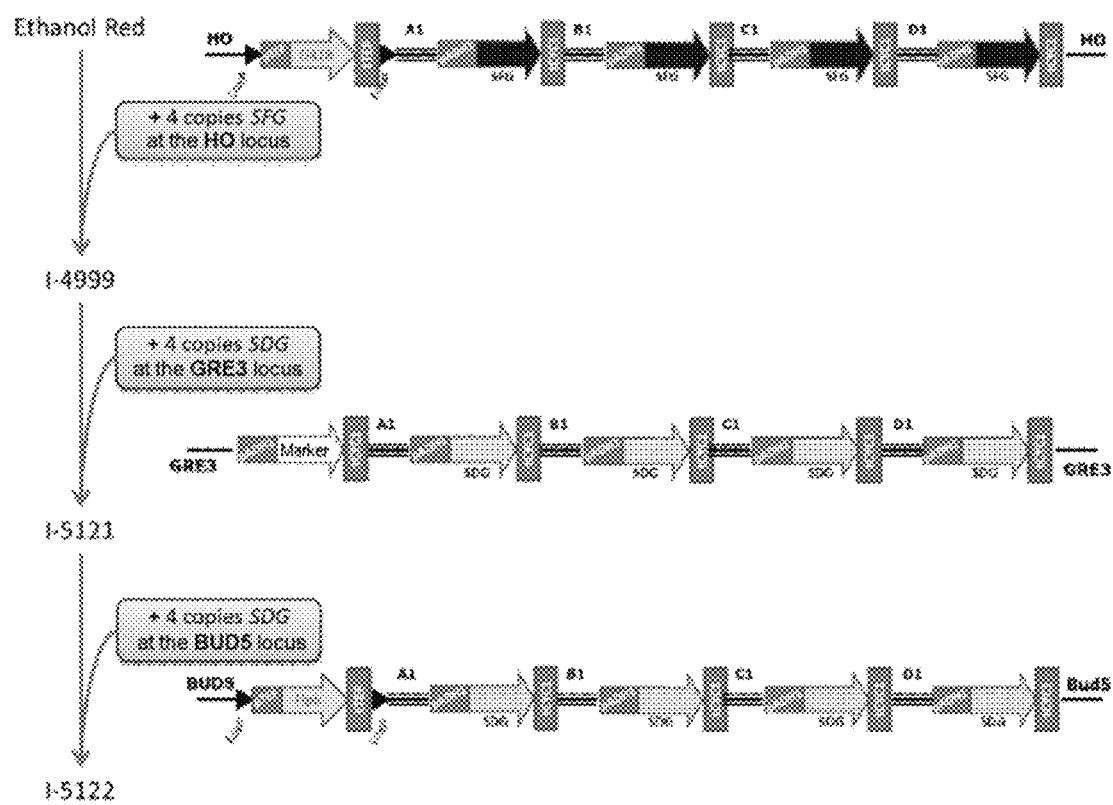

FIG. 14 describes the strategy and the various steps for obtaining the I-5121 (A) and I-5122 (B) strains.

Figure 15:
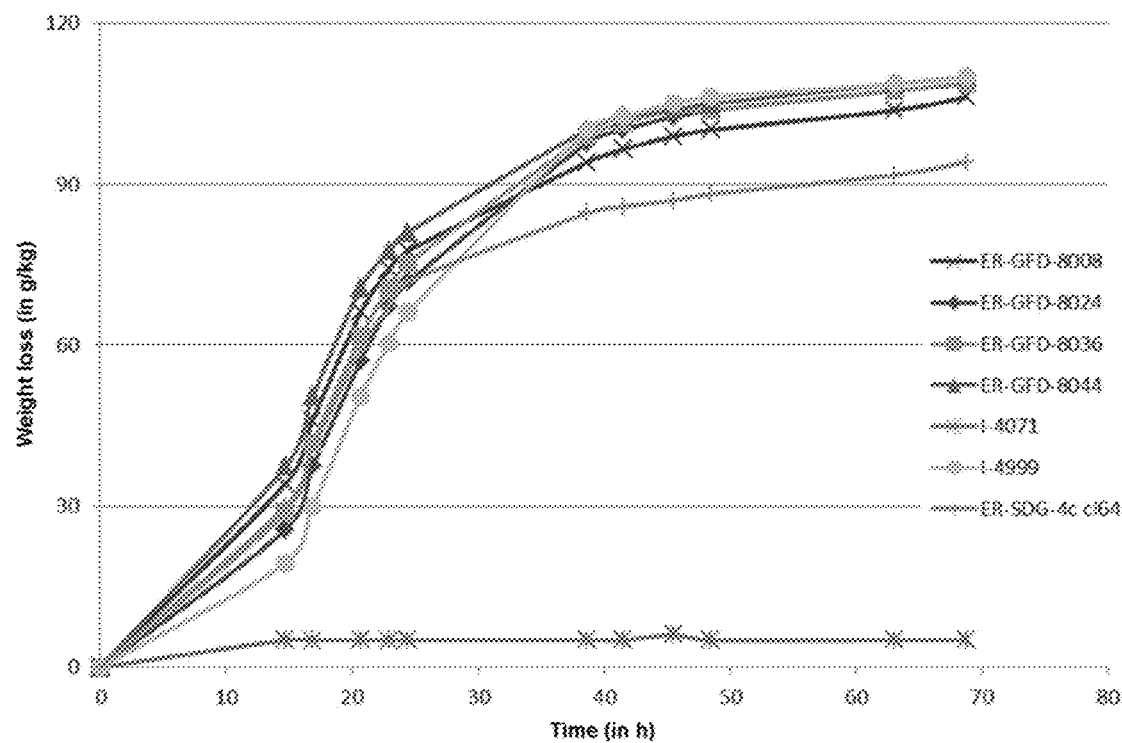

FIG. 15 represents a fermentation on dextrin medium of the best 4 ER-GFD-8000 clones screened and also of 3 control strains (I-4071, I-4999 and ER-SDG-4c). The fermentation is carried out at 32° C. and is monitored by weight loss (g/kg) for 70 h.

Figure 16:
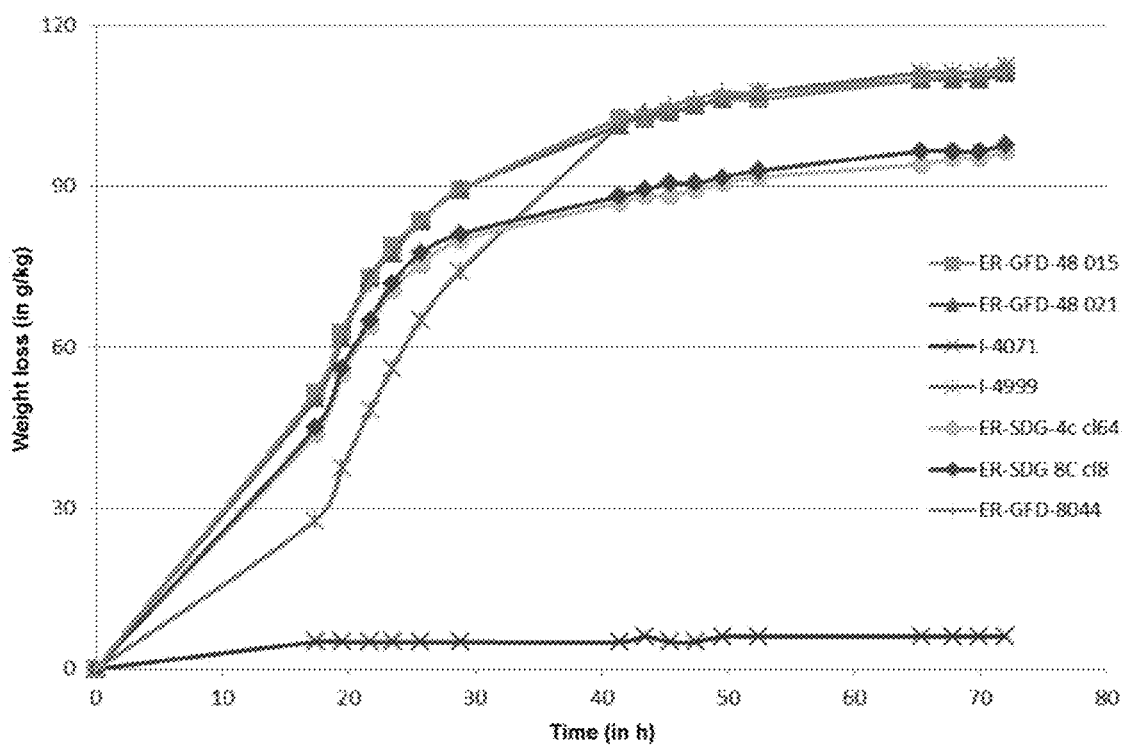

FIG. 16 represents a fermentation on dextrin medium of the best 4 ER-GFD-48000 clones screened and also of 5 control strains (I-4071, I-4999, ER-SDG-4c, ER-SDG-8c and ER-GFD-8044). The fermentation is carried out at 32° C. and is monitored by weight loss (g/kg) for 70 h.

Figure 17:
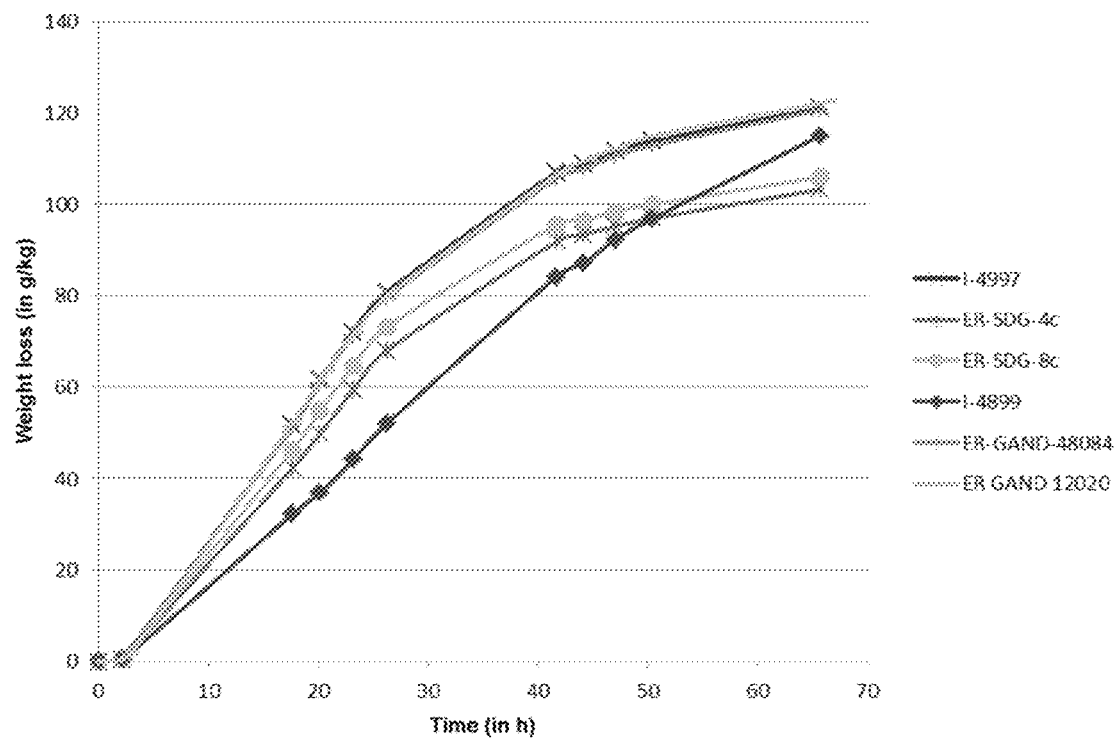

FIG. 17 represents a fermentation on industrial corn medium of the best ER-GAND clones screened and also of 4 control strains (I4899, I-4997, ER-SDG-4c and ER-SDG-8c). The fermentation is carried out at 32° C. and is monitored by weight loss (g/kg) for 70 h.

Figure 18:
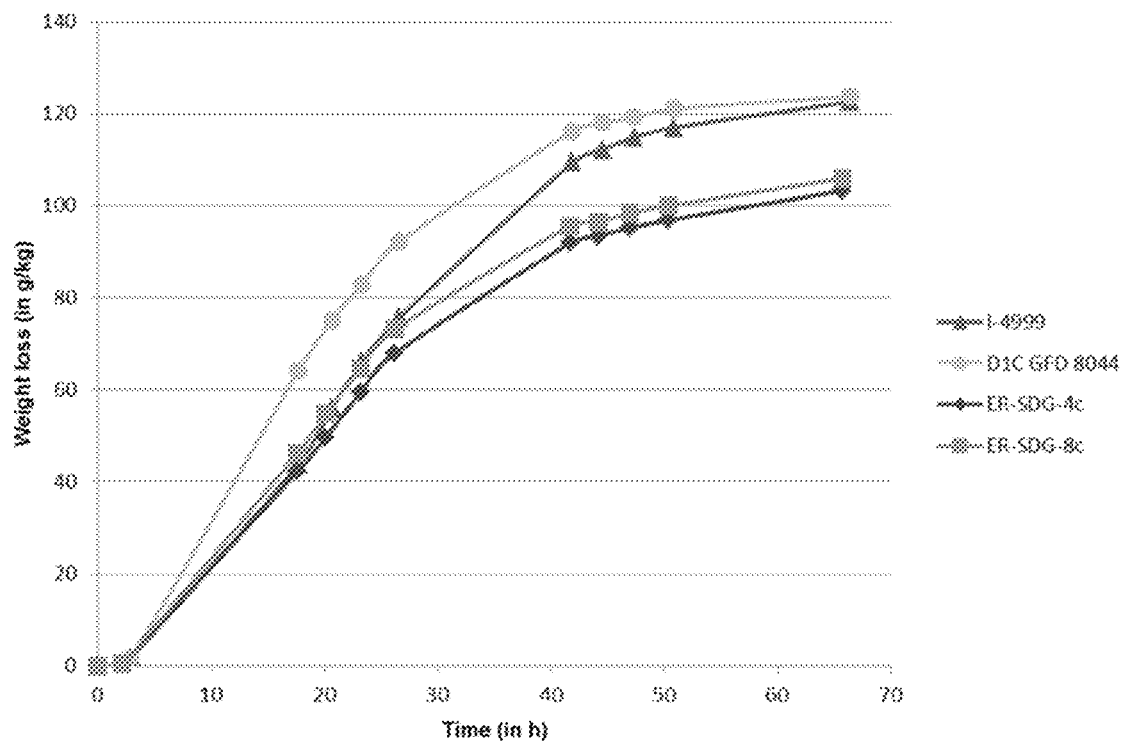

FIG. 18 represents a fermentation on industrial corn medium of the best ER-GFD series 8000 clone screened and also of 3 control strains (I-4999, ER-SDG-4c and ER-SDG-8c). The fermentation is carried out at 32° C. and is monitored by weight loss (g/kg) for 70 h.

EXAMPLES

Example 1

Integration of 4 Copies of the Gene Encoding the Glucoamylase of *Aspergillus Niger* and of at Least 3 Copies of the Gene Encoding the Glucoamylase of *Saccharomyces Cerevisiae* Var. *Diastaticus* in a *Saccharomyces Cerevisiae* Yeast Strain The copies of the genes of the glucoamylase of *Aspergillus niger* GLAA (SEQ ID No.: 1) and of the glucoamylase of *S. cerevisiae* var. *diastaticus* STA1 (SEQ ID No.: 3) were synthesized with codon usage bias for *Saccharomyces cerevisiae*.

The DNA sequences used were cloned into a standard vector comprising:
  the integration targets
  the chosen promoters/terminators, for example pADH1/tCYC1
  the resistance markers which may subsequently be removed.

In the present example, the pANG plasmid (applicant's internal name) was used to express the GLAA glucoamylase of *Aspergillus niger* (cf. FIG. 1). Likewise, the plasmid pSDG (applicant's internal name) was prepared in order to express the STA1 glucoamylase of *S. cerevisiae* var. *diastaticus*.

The principle of the cloning of 4 copies of GLAA or of at least 3 copies of STA1 can be explained in detail in the following way:
  an expression module comprising the pADH1 promoter, the ORF of the glucoamylases and the tCYC1 terminator was amplified with 3 or 4 different oligonucleotide pairs. Each module obtained after PCR amplification has these 3 elements in common.
  A selection module comprising a strong promoter/terminator, and a gene of which the expression confers, on the yeasts which contain it, a characteristic which makes it possible to select them. It is for example an antibiotic-resistance gene or a gene which allows the yeast to grow on a particular medium. Since the antibiotic-marker-resistance module is flanked by LoxP sites, it will be possible to remove it, a posteriori, through the action of the Cre recombinase.

"ORF" means "Open Reading Frame".

The primers used for the integration of the 4 copies of the GLAA gene and of the selection module at the HO locus are the following:

```
1f-Gibson AMG:
                                           (SEQ ID No.: 5)
TCTGATGGCTAACGGTGAAATTAAAGACATCGCAAACGTCACGGCTAACT
TGAAGCTTCGTACGCTGCAGG A1-Gibson AMG:
                                           (SEQ ID No.: 6)
TCACTGTACGGTGAGAACGTAGATGGTGTGCGCATAGGCCACTAGTGGAT
CT A2-Gibson AMG:
                                           (SEQ ID No.: 7)
CACACCATCTACGTTCTCACCGTACAGTGAGCATAACCGCTAGAGTACTT B1-Gibson AMG:
                                           (SEQ ID No.: 8)
TTACGTAGACTGAGTAGCAACGGTTGAGGACAGCTTGCAAATTAAAGCCT B2-Gibson AMG:
                                           (SEQ ID No.: 9)
TCCTCAACCGTTGCTACTCAGTCTACGTAAGCATAACCGCTAGAGTACTT C1-Gibson AMG:
                                           (SEQ ID No.: 10)
TCAGTAGCACAGAGAAGTGTAGGAGTGTAGCAGCTTGCAAATTAAAGCCT C2-Gibson AMG:
                                           (SEQ ID No.: 11)
CTACACTCCTACACTTCTCTGTGCTACTGAGCATAACCGCTAGAGTACTT D1-Gibson AMG:
                                           (SEQ ID No.: 12)
TTAGGATACATGCAGTAGACGAGGTAAGCACAGCTTGCAAATTAAAGCCT D2-Gibson AMG:
                                           (SEQ ID No.: 13)
TGCTTACCTCGTCTACTGCATGTATCCTAAGCATAACCGCTAGAGTACTT 2r-Gibson AMG:
                                           (SEQ ID No.: 14)
ACATACTTGCAATTTATACAGTGATGACCGCTGAATTTGTATCTTCCATA
CAGCTTGCAAATTAAAGCCT.
```

The primers used for the integration of at least 3 copies of the STA1 gene and of the selection module at the GRE3 locus are the following:

```
MCI-pADH1-GRE3-f:
                                           (SEQ ID No.: 15)
TAAGGGATATAGAAGCAAATAGTTGTCAGTGCAATCCTTCAAGACGATTG
GCATAACCGCTAGAGTACTT

A1-tCYC1-r:
                                           (SEQ ID No.: 21)
TCACTGTACGGTGAGAACGTAGATGGTGTGCAGCTTGCAAATTAAAGCCT

A2-Gibson AMG:
                                           (SEQ ID No.: 7)
CACACCATCTACGTTCTCACCGTACAGTGAGCATAACCGCTAGAGTACTT B1-Gibson AMG:
                                           (SEQ ID No.: 8)
TTACGTAGACTGAGTAGCAACGGTTGAGGACAGCTTGCAAATTAAAGCCT B2-Gibson AMG:
                                           (SEQ ID No.: 9)
TCCTCAACCGTTGCTACTCAGTCTACGTAAGCATAACCGCTAGAGTACTT
```

-continued

C1-Gibson AMG:
(SEQ ID No.: 10)
TCAGTAGCACAGAGAAGTGTAGGAGTGTAGCAGCTTGCAAATTAAAGCCT C2-Gibson AMG:
(SEQ ID No.: 11)
CTACACTCCTACACTTCTCTGTGCTACTGAGCATAACCGCTAGAGTACTT D1-Gibson AMG:
(SEQ ID No.: 12)
TTAGGATACATGCAGTAGACGAGGTAAGCACAGCTTGCAAATTAAAGCCT D2-Gibson AMG:
(SEQ ID No.: 13)
TGCTTACCTCGTCTACTGCATGTATCCTAAGCATAACCGCTAGAGTACTT MCI-tCYC1-GRE3-r:
(SEQ ID No.: 16)
CACATATACAGCATCGGAATGAGGGAAATTTGTTCATATCGTCGTTGAGT
CAGCTTGCAAATTAAAGCCT.

Table 1 mentions the oligonucleocide pairs used in the selection and expression modules.

TABLE 1

Primer pairs used for the cloning of 4 copies of GLAA and for example 3 and 4 copies of STA1

| | Selection module primer pairs | Expression module primer pairs for the cloning of 4 copies of GLAA and 4 copies of STA1 | Expression module primer pairs for the cloning of 4 copies of GLAA and 3 copies of STA1 |
|---|---|---|---|
| Primers for cloning the ANG gene | 1f-Gibson AMG + A1-Gibson AMG | A2-Gibson AMG + B1-Gibson AMG<br>B2-Gibson AMG + C1-Gibson AMG<br>C2-Gibson AMG + D1-Gibson AMG<br>D2-Gibson AMG + 2r-Gibson AMG | A2-Gibson AMG + B1-Gibson AMG<br>B2-Gibson AMG + C1-Gibson AMG<br>C2-Gibson AMG + D1-Gibson AMG<br>D2-Gibson AMG + 2r-Gibson AMG |
| Primers for cloning the SDG gene | MCI-pADH1-GRE3-f + A1-tCYC1-r | A2-Gibson AMG + B1-Gibson AMG<br>B2-Gibson AMG + C1-Gibson AMG<br>C2-Gibson AMG + D1-Gibson AMG<br>D2-Gibson AMG + MCI-tCYC1-GRE3-r | A2-Gibson AMG + B1-Gibson AMG<br>B2-Gibson AMG + C1-Gibson AMG<br>C2-Gibson AMG + MCI-tCYC1-GRE3-r |

"ANG gene" means GLAA gene of the glucoamylase of *Aspergillus niger*.

"SDG gene" means STA1 gene of the glucoamylase of *Saccharomyces cerevisiae* var. *diastaticus*.

Each amplified module has recombinogenic sequences (A1, B1, C1 and D1) on either side of its promoter and of its terminator. These sequences are introduced by the floating tails of the PCR primers and will make it possible for the modules to align and to recombine specifically by homology between these recombinogenic sequences (FIG. 2).

The strategy employed consists in simultaneously integrating several glucoamylase gene expression modules into an *S. cerevisiae* strain in a single step at a given locus, using as a basis the natural capacity of the yeast to perform homologous recombination in vivo.

Depending on the combinations of PCR products prepared, at least three glucoamylase expression modules and one selection module can be transformed into the *S. cerevisiae* strain.

The selection of the clones having correctly integrated the expression cassettes is carried out firstly on the basis of the presence of the selection module in the integration cassette (MCI).

The presence of homologous sequences at a given locus, for example the HO locus, at the 5' and 3' ends of the multi-integrative expression cassette allows the simultaneous integration of the expression modules and of the selection module by homologous recombination at this given locus.

The use of various selectable markers and of their recycling and also the integration at various loci allows the sequential and repeated integration of several multi-integrative cassettes.

For example, FIG. 3 shows the various steps for obtaining the I-5005 strain as explained below.

1-integration of 4 expression modules for the glucoamylase of *A. niger*, hereinafter GLAA, and of the G418 selection module (geneticin-resistance gene/KanMX marker) at the HO locus then making it possible to obtain the ER-ANG-G418 strain;

2-removal of the selection module through the action of the Cre recombinase enabling the selection of the strain deposited, on Oct. 15, 2014, at the CNCM under number I-4899;

3-integration of a second cassette composed of several expression modules for the glucoamylase of *S. cerevisiae* var. *diastaticus*, hereinafter STA1, at the GRE3 locus.

The strains jointly expressing the glucoamylases of *A. niger* (GLAA) and of *S. cerevisiae* var. *diastaticus* (STA1) were called ER-GAND. According to this construction model, it is thus possible to construct yeasts that have integrated at least 4 copies of the GLAA glucoamylase gene and at least 3 copies of the STA1 glucoamylase gene.

For the ER-GAND yeasts, two series of clones were generated. The 7000 series (ER-GAND-7200 to ER-GAND-7376) corresponds to the integration of 4 copies of the GLAA glucoamylase gene (of *A. niger*) and 3 copies of the STA1 glucoamylase gene (of *S. cerevisiae* var. *diastaticus*). With regard to the 8000 series (ER-GAND-8000 to ER-GAND-8159), at least 4 copies of the GLAA glucoamylase gene (of *A. niger*) and 4 copies of the STA1 glucoamylase gene (of *S. cerevisiae* var. *diastaticus*) were cloned. The 8159 clone corresponds to the I-4997 strain.

The yeast strains used are recalled below in table 2, along with their characteristics.

TABLE 2

Summary of the names/numbers
of strains and of the number of copies
of glucoamylase genes integrated

| Strain name | CNCM | ANG GA - Copies | GA of SDG Copies | GA of SFG Copies |
|---|---|---|---|---|
| ER | I-4071 | 0 | 0 | 0 |
| ER-ANG-G418 | nd | 4 | 0 | 0 |
| ER-GA-36 | I-4899 | 4 | 0 | 0 |
| ER-SFG-4c | I-4999 | 0 | 0 | 4 |
| ER-SDG-3c | I-4998 | 0 | 3 | 0 |

(nd: not deposited)

Example 2

Screening of the Strains

Three phenotypic screenings were carried out in order to select the best fifteen clones most effective for the intended application.

a) Phenotypic Screening with Iodine

The hydrolysis of the soluble starch by the yeast transformants is tested on a YEG/starch agar medium (1% glucose, 0.5% yeast extract, 1% soluble starch). The yeast cells are deposited on the YEG/starch agar and incubated for 2 days at 30° C. The dishes are then stained with iodine vapor in order to visualize the hydrolysis halos present around the yeast colonies.

This screening with iodine vapor makes it possible to select the clones secreting at least one enzyme capable of hydrolyzing the starch. These positive clones can be visualized in particular by hydrolysis halos, the size of which is proportional to the enzymatic activity. FIG. 4 shows an example of screening 88 ER-GAND clones on YEG/starch medium after iodine staining. Table 3 presents the results obtained after iodine staining.

TABLE 3

Results of the screening with iodine
for the 2 ER-GAND series

| ER-GAND strains | Number of clones screened | Growth on YEG | No hydrolysis phenotype | Hydrolysis phenotype weaker than the control |
|---|---|---|---|---|
| Series 7000 | 176 | 173 (98%) | 1 (<1%) | 0 (0%) |
| Series 8000 | 176 | 176 (100%) | 5 (3%) | 1 (<1%) |

Out of 176 clones screened for each series, less than 3% of the clones tested do not appear to be capable of hydrolyzing the starch under the culture conditions of the example. It should be noted that the host strain used in this strategy already had several glucoamylase genes in its genome, thus a hydrolysis halo is present for this strain. These "negative" clones therefore appear to have lost their glucoamylase genes.

b) Phenotypic Screening by Fermentation in a Medium of 0.5 g

The phenotypic screening on a dextrin medium under fermentation conditions makes it possible to eliminate the ER-GAND clones that cannot ferment or that ferment more slowly than the I-4899 strain. For this, visual monitoring of the biomass during the fermentation is carried out twice a day for 3 days. By comparing the rate of appearance of the biomass pellet with respect to the I-4999 and I-4998 control strains, the most promising strains can then be selected.

The ER-SDG-1c strain mentioned in the controls of FIG. 5 is an Ethanol Red® strain expressing a copy of the glucoamylase gene of S. cerevisiae var. diastaticus (STA1).

The GO-ANG-4c strain mentioned in the controls of FIG. 5 is a GenOne+® strain deposited, on Jul. 25, 2013, at the CNCM under number I-4791 expressing four copies of the glucoamylase gene of A. niger (GLAA).

The fermentation medium used, in the dextrin medium, is a synthetic medium containing starch dextrins (220 g/kg), yeast extract (5 g/kg), urea (2 g/kg), $KH_2PO_4$ (1 g/kg) and also minerals and vitamins. The strains which ferment the most quickly are strains capable of secreting a considerable amount of glucoamylase, therefore making it possible to release glucose by hydrolysis of the dextrin molecules. The glucose thus released is then metabolized by the S. cerevisiae yeast in order to product ethanol.

FIG. 5 illustrates an example of fermentation in plates for the 88 ER-GAND clones. The biomass pellets correspond to a fermentation of 31 h on dextrin medium. The clones indicated by an arrow show a larger biomass pellet than for the I-4899 strain. These are the clones that were selected to be tested in a fermentation on 100 g of dextrin medium.

For each ER-GAND series, fifteen clones were selected and will be tested in a fermentation on 100 g of dextrin medium.

c) Phenotypic screening by fermentation in a medium of 100 g

A fermentation on 100 g of selective synthetic dextrin medium (corn dextrin 220 g/kg, yeast extract 5 g/kg, urea 2 g/kg, $KH_2PO_4$ 1 g/kg and also minerals and vitamins) is carried out at 32° C. The dextrins are starch hydrolysates which make it possible to mimic the real medium.

The S. cerevisiae strains modified according to the invention were pre-propagated on a YPG (Yeast extract, Peptone, Glucose) medium for 24 h at 30° C. The initial pH of the fermentation medium was adjusted to 5.0 without regulation. The fermentation medium was then inoculated at a level of 0.125 g equivalent dry matter per kilogram of medium. No exogenous hydrolysis enzyme is added to the fermentation medium. Monitoring by weight loss was carried out for 72 hours and is shown in FIG. 6.

In this type of fermentation medium (dextrin), little glucose is free at t0 (approximately ten or so grams). Since the ER strain does not have an enzyme that can hydrolyze the dextrins, it consumes only the available glucose and therefore a low weight loss is measured (approximately 5 g/kg).

On the basis of the weight loss monitoring results presented in FIG. 6, out of 30 clones tested, 3 groups can be established according to their kinetic behaviors in fermentation:

Group A: 4 clones have a kinetics profile identical to the I-4899 mother yeast strain.

Group B: 2 clones exhibit a kinetics profile similar to the I-4999 reference strain.

Group C: the fermentation kinetics performance of 24 clones is better than that of the I-4999 strain (target performance).

Among the strains of group C, the best 5 clones of each series (series 7000 and 8000) were selected to be tested on an industrial medium under real biofuel production conditions.

Example 3

Evaluation of the Production of Enzymatic Activity of the Strains

The 5 ER-GAND clones with 4 copies of GLAA and 3 copies of STA1 (series 7000) previously selected were evaluated at 32° C. on the E140723-11 industrial medium and compared with the I-4998, I-4999 and I-4899 control strains. They were the following clones: 7215, 7250, 7271, 7296, 7302. The 7302 clone corresponds to the I-5005 strain.

The strain (deposited, on Jul. 9, 2015, at the CNCM under number I-4998) expressing the STA1 activity derived from *S. cerevisiae* var. *diastaticus* made it possible to obtain rapid but incomplete dextrin hydrolysis kinetics, whereas the strain (I-4899) expressing the GLAA activity derived from *A. niger* made it possible to obtain a dextrin hydrolysis which was satisfactory but had kinetics that were not as good as I-4998.

The strains were pre-propagated on a medium/water mixture (70%/30%) for 7 h 30 at 32° C. The propagation medium was then transferred to the fermentation medium at a level of 2.5%/97.5%. The fermentation was carried out at 32° C. The initial pH of the propagation and fermentation media was adjusted to 5.0 without regulation. Urea was added in propagation (1500 ppm) and in fermentation (1000 ppm). A dose of 0.06 ml/kg of Spirizyme® Ultra (Novozyme) commercial GA glucoamylase solids was added in propagation but not in fermentation.

The weight loss of the fermentation reactors was measured over time from t=0 to t=71 h.

The results of weight losses obtained during the alcoholic fermentation are presented in FIG. 7.

FIG. 7 shows that the new strains make it possible to obtain a dextrin hydrolysis that is both as fast as the I-4998 strain and as complete as the I-4899 strain, but that they are also faster than the I-4999 strain. It can be concluded from this that the production of glucoamylase of *Saccharomyces cerevisiae* var. *diastaticus* has a stimulating effect on the hydrolytic activity of the *Aspergillus niger* glucoamylase. These strains merely exhibit a combination of the characteristics of the fungal glucoamylase of *Aspergillus niger* and of the glucoamylase of *Saccharomyces cerevisiae* var. *diastaticus* (that is to say with a kinetics profile which would be between that of the glucoamylase of *Aspergillus niger* and that of the glucoamylase of *Saccharomyces cerevisiae* var. *diastaticus*), but exhibit an improved kinetics profile with an acceleration of the kinetics. There therefore appears to be a synergistic effect between the glucoamylase of fungal origin and that of *Saccharomyces cerevisiae* var. *diastaticus*.

The composition of the fermentation samples is measured by high performance liquid chromatography (HPLC) on an Aminex® HPX 87H column (Biorad) with a 5 mM H2SO4 solution as eluent.

The HPLCs carried out at the end of fermentation do not show any major defect for any of the strains in question (table 4). They indeed recall the incapacity of the STA1 enzyme to totally hydrolyze dextrins, contrary to the SFG and GLAA enzymes.

TABLE 4

| | Concentrations after 71 H of fermentation (g/kg) | | | | | |
|---|---|---|---|---|---|---|
| | Total sugars (g/kg) | Free glucose (g/kg) | Free sugars (g/kg) | Glycerol (g/kg) | Acetic acid (g/kg) | Ethanol (g/kg) |
| T0 | 232.6 | 9.4 | 11.7 | 1.3 | 0.7 | 2.0 |
| ER-GAND-7215 | 11.3 | 0.2 | 1.3 | 8.2 | 0.3 | 120.7 |
| ER-GAND-7250 | 9.9 | 0.1 | 1.3 | 8.1 | 0.2 | 122.2 |
| ER-GAND-7271 | 12.6 | 0.2 | 1.3 | 8.1 | 0.2 | 121.5 |
| ER-GAND-7296 | 10.7 | 0.2 | 1.3 | 8.4 | 0.2 | 121.3 |
| I-5005 | 10.9 | 0.1 | 1.2 | 8.4 | 0.2 | 122.1 |
| I-4998 | 37.3 | 0.8 | 1.8 | 6.7 | 0.0 | 108.7 |
| I-4999 | 11.7 | 0.2 | 1.1 | 8.8 | 0.2 | 120.1 |
| I-4899 | 12.1 | 0.3 | 1.6 | 8.4 | 0.3 | 119.1 |

Example 4

Integration of 4 Additional Copies of a Gene Encoding a Glucoamylase in a *Saccharomyces Cerevisiae* Yeast Strain Possessing at Least 4 Copies of the Gene Encoding the Glucoamylase of *Aspergillus Niger* and at Least 4 Copies of the Gene Encoding the Glucoamylase of *Saccharomyces Cerevisiae* Var. *Diastaticus*

Using the ER-GAND-8159 clone (CNCM I-4997), additional copies of the gene of a glucoamylase were integrated into the BUD5 locus in order to increase the number of copies of the gene of one of the two glucoamylases.

In the present example, the sequences used for this integration correspond to the genes of the glucoamylase of *Aspergillus niger* GLAA (SEQ ID No.: 1) and of the glucoamylase of *S. cerevisiae* var. *diastaticus* STA1 (SEQ ID No.: 3) previously described.

The general principle of the cloning is the same as that described in example 1, only the integration locus varies.

The principle of the cloning of 4 additional copies of GLAA or of 4 additional copies of STA1 can be described in detail in the following way:

an expression module comprising the pADH1 promoter, the ORF of the glucoamylases and the tCYC1 terminator was amplified with 4 different oligonucleotide pairs. Each module obtained after PCR amplification has these 3 elements in common.

A selection module comprising a strong promoter/terminator, and a gene of which the expression confers, on the yeasts which contain it, a characteristic which makes it possible to select them. It is for example an antibiotic-resistance gene or a gene which allows the yeast to grow on a particular medium. Since the antibiotic-marker-resistance module is flanked by LoxP sites, it will be possible to remove it, a posteriori, through the action of the Cre recombinase.

*Saccharomyces cerevisiae* yeast strains expressing exclusively either the glucoamylase of *A. niger* or the glucoamylase of *S. cerevisiae* var. *diastaticus* were also obtained according to the same cloning strategy. These *S. cerevisiae* yeast strains can then contain 4 or 8 copies of the gene of the same glucoamylase in one locus or both loci.

The primers used for the integration of the various copies of the GLAA gene or of the STA1 gene and of the selection module are the following:

MCI-pADH1-BUD5-f:

(SEQ ID No.: 19)
CGCTCCAGAATTAGCGGACCTCTTGAGCGGTGAGCCTCTGGCAAAGAAGA
GCATAACCGCTAGAGTACTT

MCI-pTEF-BUD51:

(SEQ ID No.: 20)
CGCTCCAGAATTAGCGGACCTCTTGAGCGGTGAGCCTCTGGCAAAGAAGA
TGAAGCTTCGTACGCTGCAGG

MCI-pADH1-GRE3-f:

(SEQ ID No.: 15)
TAAGGGATATAGAAGCAAATAGTTGTCAGTGCAATCCTTCAAGACGATTG
GCATAACCGCTAGAGTACTT

A1-tCYC1-r:

(SEQ ID No.: 21)
TCACTGTACGGTGAGAACGTAGATGGTGTGCAGCTTGCAAATTAAAGCCT

A2-Gibson AMG:

(SEQ ID No.: 7)
CACACCATCTACGTTCTCACCGTACAGTGAGCATAACCGCTAGAGTACTT

B1-Gibson AMG:

(SEQ ID No.: 8)
TTACGTAGACTGAGTAGCAACGGTTGAGGACAGCTTGCAAATTAAAGCCT

B2-Gibson AMG:

(SEQ ID No.: 9)
TCCTCAACCGTTGCTACTCAGTCTACGTAAGCATAACCGCTAGAGTACTT

C1-Gibson AMG:

(SEQ ID No.: 10)
TCAGTAGCACAGAGAAGTGTAGGAGTGTAGCAGCTTGCAAATTAAAGCCT

C2-Gibson AMG:

(SEQ ID No.: 11)
CTACACTCCTACACTTCTCTGTGCTACTGAGCATAACCGCTAGAGTACTT

D1-Gibson AMG:

(SEQ ID No.: 12)
TTAGGATACATGCAGTAGACGAGGTAAGCACAGCTTGCAAATTAAAGCCT

D2-Gibson AMG:

(SEQ ID No.: 13)
TGCTTACCTCGTCTACTGCATGTATCCTAAGCATAACCGCTAGAGTACTT

MCI-tCYC1-BUD5-r:

(SEQ ID No.: 22)
CTCAAGAACGTAGGACGATAACTGGTTGGAAAGCGTAAACACGGAGTCAA
CAGCTTGCAAATTAAAGCCT

MCI-tCYC1-GRE3-r:

(SEQ ID No.: 16)
CACATATACAGCATCGGAATGAGGGAAATTTGTTCATATCGTCGTTGAGT
CAGCTTGCAAATTAAAGCCT.

Table 5 mentions the oligonucleotide pairs used in the selection and expression modules, and also the host yeast strain for the various constructions

TABLE 5

Primer pairs used for the cloning of 4 copies of GLAA and for example 4 copies of STA1 in the BUD5 locus

| | Constructions | | | | |
|---|---|---|---|---|---|
| | 1 | 2 | 3 | 4 | 5 |
| Host S. cerevisiae strains | ER-GAND-8159 I-4997 | ER-GAND-81591-4997 | ER-GA-36 1-4899 | Ethanol Red 1-4071 | ER-SDG-4c |
| Integration locus | | BUD5 | | GER3 | BUD5 |
| Selection module | MCI-pADH1-BUD5-f A1-tCYC1-r | | | MCI-pADH1-GRE3-f A1-tCYC1-r | MCI-pTEF-BUD5-f A1-tCYC1-r |
| Module 1 | | A2-Gibson AMG B1-Gibson AMG | | | |
| Module 2 | | B2-Gibson AMG C1-Gibson AMG | | | |
| Module 3 | | C2-Gibson AMG D1-Gibson AMG | | | |
| Module 4 | D2-Gibson AMG MCI-tCYC1-BUD5-r | | | D2-Gibson AMG MCI-tCYC1-GRE3-r | D2-Gibson AMG MCI-tCYC1-BUD5-r |
| Name of S. cerevisiae strains obtained | ER-GAND-12020 (I-5119) | ER-GAND-48038 (I-5120) | ER-ANG-8c | ER-SDG-4c | ER-SDG-8c |

The strategy is strictly similar to that employed in example 1 for the simultaneous integration of several glucoamylase gene expression modules in an *S. cerevisiae* strain in a single step at a given locus, using, as a basis, the natural capacity of the yeast to perform homologous recombination in vivo.

The strains jointly expressing the glucoamylases of *A. niger* (GLAA) and of *S. cerevisiae* var. *diastaticus* (STA1) were called ER-GAND plus the number of the clone. Two series of clones were generated. The 12000 series (ER-GAND-12001 to 12023) corresponds to the integration of 8 copies of the GLAA glucoamylase gene (of *A. niger*) and 4 copies of the STA1 glucoamylase gene (of *S. cerevisiae* var. *diastaticus*) and the 48000 series (ER-GAND-480001 to 480088) corresponds to the integration of 4 copies of the GLAA glucoamylase gene (of *A. niger*) and 8 copies of the STA1 glucoamylase gene (of *S. cerevisiae* var. *diastaticus*).

The strains expressing exclusively the glucoamylase of *A. niger* (GLAA) were called ER-ANG-z-c where z corresponds to the copy number of the GLAA gene introduced into the host strain. The strains expressing exclusively the *S. cerevisiae* var. *diastaticus* glucoamylase (STA1) were called ER-SDG-y-c where y corresponds to the copy number of the STA1 gene introduced into the host strain.

For example, FIGS. 8 to 10 show the various steps for obtaining the ER-GAND-12000, ER-GAND-48000, ER-ANG-8c, ER-SDG-4c and ER-SDG-8c strains constructed in this example.

The yeast strains used are recalled below in table 6 along with their characteristics.

TABLE 6

Summary of the strain names/numbers and of the number of copies of glucoamylase genes integrated

| Strain name | CNCM | GA-ANG Copies | GA of SDG Copies |
|---|---|---|---|
| ER | I-4071 | 0 | 0 |
| ER-GA-36 | I-4899 | 4 | 0 |
| ER-SDG-4c | nd | 0 | 4 |
| ER-SDG-8c | nd | 0 | 8 |
| ER-ANG-8c | nd | 8 | 4 |
| ER-GAND-12020 | I-5119 | 8 | 4 |
| ER-GAND-48035 | I-5120 | 4 | 8 |

(nd: not deposited)

Example 5

Screening of the Strains

Three phenotypic screenings were carried out in order to select the best clones that are the most effective for the intended application.

a) Phenotypic Screening with Iodine

The phenotypic screening with iodine was carried out in a manner identical to example 2a). Table 7 presents the results obtained after iodine staining.

TABLE 7

Results of the screening with iodine for the 5 series of cloning carried out. The weaker hydrolysis phenotype corresponds to a halo around the clone that is smaller than that of the host *S.cerevisiae* strain

| S.cerevisiae strains | Number of clones screened | Growth on YEG | No hydrolysis phenotype | Weaker hydrolysis phenotype* |
|---|---|---|---|---|
| ER-ANG-8c | 88 | 0 | 0 | 0 |
| ER-SDG-4c | 132 | 0 | 3 (2%) | — |
| ER-SDG-8c | 9 | 0 | 0 | 0 |
| ER-GAND 12000 series | 23 | 0 | 0 | 1 (4%) |
| ER-GAND 48000 series | 88 | 0 | 0 | 0 |

Out of all the 5 series of screening carried out, only the series for ER-SDG-4c provides any clones that do not have starch hydrolysis activity under the culture conditions of the example. It should be noted that this is the only series where the cloning was carried out in the Ethanol Red® host strain which does not possess a glucoamylase gene. These "negative" clones therefore appear not to have integrated at least one glucoamylase gene.

b) Phenotypic Screening by Fermentation in a Medium of 0.5 g

The phenotypic screening on a dextrin medium under fermentation conditions makes it possible to eliminate the clones obtained in the various series which cannot ferment or which ferment more slowly than the corresponding host strain. For this, visual monitoring of the biomass during the fermentation is carried out twice a day for 2 days. By comparing the rate of appearance of the biomass pellet with respect to the I-4997 control strain, the most promising strains can then be selected.

The fermentation medium used, which is the dextrin medium, is a synthetic medium containing starch dextrins (220 g/kg), yeast extract (5 g/kg), urea (2 g/kg), $KH_2PO_4$ (1 g/kg) and also minerals and vitamins. The strains which ferment the most quickly are strains capable of secreting a large amount of glucoamylase therefore making it possible to release glucose by hydrolysis of the dextrin molecules. The glucose thus released is then metabolized by the *S. cerevisiae* yeast in order to produce ethanol.

For each cloning series, between two and four clones were selected and are tested on a larger scale in a fermentation on 100 g of dextrin medium.

c) Phenotypic Screening by Fermentation in a Medium of 100 g

As for example 2c), a fermentation on 100 g of selective synthetic dextrin medium (corn dextrin 220 g/kg, yeast extract 5 g/kg, urea 2 g/kg, $KH_2PO_4$ 1 g/kg and also minerals and vitamins) is carried out at 32° C. The dextrins are starch hydrolysates which make it possible to mimic the real medium.

The *S. cerevisiae* strains modified according to the invention were pre-propagated on a YPG (Yeast extract, Peptone, Glucose) medium for 24 h at 30° C. The initial pH of the fermentation medium was adjusted to 5.0 without regulation. The fermentation medium was then inoculated at a level of 0.125 g equivalent dry matter per kilogram of medium. No exogenous hydrolysis enzyme is added to the fermentation medium. Weight loss monitorings were carried out for 72 hours and are shown in FIG. 11, for the ER-GAND-12000 series, and FIG. 12 for the ER-GAND-48000 series.

In this type of fermentation medium (dextrin), little glucose is free at t0 (approximately ten or so grams). Since the ER strain does not have any enzyme that can hydrolyze dextrins, it consumes only the available glucose and a low weight loss is therefore measured (approximately 5 g/kg) from 14 h up to the end of the fermentation.

On the basis of the weight loss monitoring results presented in FIGS. 11 and 12, the 3 clones tested for each series exhibit weight-loss kinetics that are virtually identical and therefore appear to be equivalent in terms of fermentation performance on a dextrin medium.

The increase in the copy number of the STA1 or sGLAA gene (from 4 to 8 copies) in an *S. cerevisiae* strain also makes it possible to gain in kinetic performance, in particular for the fermentation rate during the first 30 hours (FIG. 11).

The addition, likewise, of either 4 copies of the sGLAA gene (FIG. 11) or of 4 copies of the STA1 gene (FIG. 12) in the ER-GAND-8159 strain (I-4997) allows an improvement in the fermentation kinetics on dextrin medium and thus makes it possible to combine the performance levels of the glucoamylases of *S. cerevisiae* var. *diastaticus* and of *A. niger*.

Example 6

Integration of 4 or 8 Copies of the Gene Encoding the Glucoamylase of *Saccharomyces Cerevisiae* Var. *Diastaticus* into a *Saccharomyces Cerevisiae* Yeast Strain Containing 4 Copies of the Gene Encoding the Glucoamylase of *Saccharomycopsis Fibuligera*

The copies of the genes of the glucoamylase of *S. cerevisiae* var. *diastaticus* STA1 (SEQ ID No.: 3) and of the glucoamylase of *Saccharomycopsis fibuligera* GLU0111 (SEQ ID No.: 17) were synthesized with codon usage bias for *Saccharomyces cerevisiae*.

The DNA sequences used were cloned into a standard vector comprising:
- the integration targets
- the chosen promoters/terminators, for example pADH1/tCYC1
- the resistance markers which may be subsequently removed.

In the present example, the pSFG plasmid (applicant's internal name) was used to express the GLU0111 glucoamylase of *Saccharomycopsis fibuligera* (cf. FIG. 13). Likewise, the pSDG plasmid (applicant's internal name) is prepared in order to express the STA1 glucoamylase of *S. cerevisiae* var. *diastaticus*.

The principle of the cloning of 4 copies of GLU0111 or of 4 or 8 copies of STA1 can be described in detail in the following way:
- an expression module comprising the pADH1 promoter, the ORF of the glucoamylases and the tCYC1 terminator was amplified with 3 or 4 different oligonucleotide pairs. Each module obtained after PCR amplification has these 3 elements in common.
- A selection module comprising a strong promoter/terminator, and a gene of which the expression confers, on the yeasts which contain it, a characteristic which makes it possible to select them. It is for example an antibiotic-resistance gene or a gene which allows the yeast to grow on a particular medium. Since the antibiotic-marker-resistance module is flanked by LoxP sites, it will be possible to remove it, a posteriori, through the action of the Cre recombinase.

The primers used for the integration of the various copies of the GLAA gene or of the STA1 gene and of the selection module are the following:

```
1f-Gibson AMG:
                                          (SEQ ID No.: 5)
TCTGATGGCTAACGGTGAAATTAAAGACATCGCAAACGTCACGGCTAACT
TGAAGCTTCGTACGCTGCAGG MCI-pTEF-BUD5-f
                                          (SEQ ID No.: 20)
CGCTCCAGAATTAGCGGACCTCTTGAGCGGTGAGCCTCTGGCAAAGAAGA
TGAAGCTTCGTACGCTGCAGG MCI-pADH1-GRE3-f
                                          (SEQ ID No.: 15)
TAAGGGATATAGAAGCAAATAGTTGTCAGTGCAATCCTTCAAGACGATTG
GCATAACCGCTAGAGTACTT A1-Gibson AMG:
                                          (SEQ ID No.: 6)
TCACTGTACGGTGAGAACGTAGATGGTGTGCGCATAGGCCACTAGTGGAT
CT A1-tCYC1-r:
                                          (SEQ ID No.: 21)
TCACTGTACGGTGAGAACGTAGATGGTGTGCAGCTTGCAAATTAAAGCCT A2-Gibson AMG:
                                          (SEQ ID No.: 7)
CACACCATCTACGTTCTCACCGTACAGTGAGCATAACCGCTAGAGTACTT B1-Gibson AMG:
                                          (SEQ ID No.: 8)
TTACGTAGACTGAGTAGCAACGGTTGAGGACAGCTTGCAAATTAAAGCCT B2-Gibson AMG:
                                          (SEQ ID No.: 9)
TCCTCAACCGTTGCTACTCAGTCTACGTAAGCATAACCGCTAGAGTACTT C1-Gibson AMG:
                                          (SEQ ID No.: 10)
TCAGTAGCACAGAGAAGTGTAGGAGTGTAGCAGCTTGCAAATTAAAGCCT C2-Gibson AMG:
                                          (SEQ ID No.: 11)
CTACACTCCTACACTTCTCTGTGCTACTGAGCATAACCGCTAGAGTACTT D1-Gibson AMG:
                                          (SEQ ID No.: 12)
TTAGGATACATGCAGTAGACGAGGTAAGCACAGCTTGCAAATTAAAGCCT D2-Gibson AMG:
                                          (SEQ ID No.: 13)
TGCTTACCTCGTCTACTGCATGTATCCTAAGCATAACCGCTAGAGTACTT MCI-tCYC1-BUD5-r:
                                          (SEQ ID No.: 22)
CTCAAGAACGTAGGACGATAACTGGTTGGAAAGCGTAAACACGGAGTCAA
CAGCTTGCAAATTAAAGCCT MCI-tCYC1-GRE3-r:
                                          (SEQ ID No.: 16)
CACATATACAGCATCGGAATGAGGGAAATTTGTTCATATCGTCGTTGAGT
CAGCTTGCAAATTAAAGCCT 2r-Gibson AMG:
                                          (SEQ ID No.: 14)
ACATACTTGCAATTTATACAGTGATGACCGCTGAATTTGTATCTTCCATA
CAGCTTGCAAATTAAAGCCT.
```

TABLE 8

Primer pairs used for the cloning of 4 copies of GLU0111 and for example 4 or 8 copies of STA1

| | Constructions | | |
|---|---|---|---|
| | 1 | 2 | 3 |
| Host S. cerevisiae strains | Ethanol Red I-4071 | ER-SFG I-4999 | ER-GFD-8044 (I-5121) |
| Integration locus | HO | GRE3 | BUD5 |
| Selection module | 1f-Gibson AMG A1-Gibson AMG | MCI-pADH1-GRE3-f A1-Gibson AMG | MCI-pTEF-BUD5-f A1-Gibson AMG |
| Module 1 | | A2-Gibson AMG B1-Gibson AMG | |
| Module 2 | | B2-Gibson AMG C1-Gibson AMG | |
| Module 3 | | C2-Gibson AMG D1-Gibson AMG | |
| Module 4 | D2-Gibson AMG 2r-Gibson AMG | D2-Gibson AMG MCI-tCYC1-GRE3-r | D2-Gibson AMG MCI-tCYC1-BUD5 |
| Name of the S. cerevisiae strains obtained | ER-SFG (I-4999) | ER-GFD-8044 (I-5121) | ER-GFD-48015 (I-5122) |

"SFG gene" means GLU0111 gene of the glucoamylase of *Saccharomycopsis fibuligera*.

The strategy is strictly similar to that employed in example 1 for the simultaneous integration of several glucoamylase gene expression modules into an *S. cerevisiae* strain in a single step at a given locus, using as a basis the natural capacity of the yeast to perform homologous recombination in vivo.

For example, FIG. 14 shows the various steps for obtaining the I-5122 strain as explained below:

1—integration of 4 *S. fibuligera* glucoamylase expression modules, hereinafter GLU0111, and of the G418 selection module (geneticin-resistance gene/KanMX marker) at the HO locus, therefore making it possible to obtain the ER-SFG strain;

2—integration of a second cassette composed of 4 *S. cerevisiae* var. *diastaticus* glucoamylase expression modules, hereinafter STA1, at the GRE3 locus;

3—integration of a third cassette composed of 4 *S. cerevisiae* var. *diastaticus* glucoamylase expression modules, hereinafter STA1, at the BUD5 locus.

The strains jointly expressing the glucoamylases of *S. fibuligera* (GLU0111) and of *S. cerevisiae* var. *diastaticus* (STA1) were called ER-GFD. According to this construction model, it is thus possible to construct yeasts that have integrated 4 copies of the GLU0111 glucoamylase gene and at least 4 copies of the STA1 glucoamylase gene.

For the ER-GFD yeasts, two series of clones were generated. The 8000 series (ER-GFD-8001 to ER-GFD-8045) corresponds to the integration of 4 copies of the GLU0111 glucoamylase gene (from *S. fibuligera*) and 4 copies of the STA1 glucoamylase gene (from *S. cerevisiae* var. *diastaticus*). With regard to the 48000 series (ER-GFD-48001 to ER-GFD-48015), 4 copies of the GLU0111 glucoamylase gene (from *S. fibuligera*) and 8 copies of the STA1 glucoamylase gene (from *S. cerevisiae* var. *diastaticus*) were cloned. The ER-GFD-8044 and ER-GFD-48015 clones correspond to the I-5121 and I-5122 strains, respectively.

The Yeast strains used are recalled below in table 9 alone with their characteristics.

TABLE 9

Summary of the strain names/numbers and of the number of copies of glucoamylase genes integrated

| Strain name | CNCM | GA of SDG Copies | GA of SFG Copies |
|---|---|---|---|
| ER | I-4071 | 0 | 0 |
| ER-SFG-4c | I-4999 | 0 | 4 |
| ER-GFD-8044 | I-5121 | 4 | 4 |
| ER-GFD-48015 | I-5122 | 8 | 4 |

Example 7

Screening of the Strains

Three phenotypic screenings were carried out in order to select the best clones that are the most effective for the intended application.

a) Phenotypic Screening with Iodine

The phenotypic screening with iodine was carried out in a manner identical to example 2a).

Table 10 presents the results obtained after staining with iodine.

TABLE 10

Results of the screening with iodine for the 2 series of cloning carried out. The weaker hydrolysis phenotype corresponds to a halo around the clone that is smaller than that of the host *S. cerevisiae* strain

| S.cerevisiae strains | Number of clones screened | Growth on YEG | No hydrolysis phenotype | Weaker hydrolysis phenotype* |
|---|---|---|---|---|
| ER-GFD series 8000 | 45 | 0 | 0 | 1 (2%) |
| ER-GFD series 48000 | 15 | 0 | 0 | 0 |

Out of all of the clones screened for each series, less than 2% of the clones tested do not appear to be capable of hydrolyzing the starch under the culture conditions of the example. It should be noted that the host strain used in this strategy already possessed several glucoamylase genes in its genome, thus a hydrolysis halo is present for each strain. These "negative" clones therefore appear to have lost their glucoamylase genes.

b) Phenotypic Screening by Fermentation in a Medium of 0.5 g

The phenotypic screening on a dextrin medium under fermentation conditions makes it possible to eliminate the clones obtained in the various series which cannot ferment or which ferment more slowly than the corresponding host strain. For this, visual monitoring of the biomass during the fermentation is carried out twice a day for 2 days. By comparing the rate of appearance of the biomass pellet with respect to the I-4999 strain, the most promising strains can then be selected.

The fermentation medium used, which is the dextrin medium, is a synthetic medium containing starch dextrins (220 g/kg), yeast extract (5 g/kg), urea (2 g/kg), $KH_2PO_4$ (1 g/kg) and also minerals and vitamins. The strains which ferment the most quickly are strains capable of secreting a large amount of glucoamylase, therefore making it possible to release glucose by hydrolysis of the dextrin molecules.

The glucose thus released is then metabolized by the *S. cerevisiae* yeast in order to produce ethanol.

For each cloning series, between two and four clones were selected and are tested on a larger scale in a fermentation on 100 g of dextrin medium.

c) Phenotypic Screening by Fermentation in a Medium of 100 g

As for examples 2c) and 5c), a fermentation on 100 g of selective synthetic dextrin medium (corn dextrin 220 g/kg, yeast extract 5 g/kg, urea 2 g/kg, KH$_2$PO$_4$1 g/kg and also minerals and vitamins) is carried out at 32° C. The dextrins are starch hydrolysates which make it possible to mimic the real medium.

The *S. cerevisiae* strains modified according to the invention were pre-propagated on a YPG (Yeast extract, Peptone, Glucose) medium for 24 h at 30° C. The initial pH of the fermentation medium was adjusted to 5.0 without regulation. The fermentation medium was then inoculated at a level of 0.125 g equivalent dry matter per kilogram of medium. No exogenous hydrolysis enzyme is added to the fermentation medium. Weight loss monitorings were carried out for 72 hours and are shown in FIG. 15, for the ER-GFD-8000 series, and FIG. 16 for the ER-GFD-48000 series.

In this type of fermentation medium (dextrin), little glucose is free at t0 (approximately ten or so grams). Since the ER strain has no enzyme that can hydrolyze dextrins, it consumes only the available glucose and therefore a low weight loss is measured (approximately 5 g/kg) from 14 h up to the end of the fermentation.

On the basis of the weight-loss monitoring results presented in FIGS. 15 and 16, the clones tested for each series exhibit weight-loss kinetics that are virtually identical and therefore appear to be equivalent in terms of fermentation performance on a dextrin medium.

Example 8

Evaluation of the Production of Enzymatic Activity of the Strains

The clones previously selected were evaluated at 32° C. on the E140723-11 industrial medium and compared with the I-4998, I-4999, I-4899, I-4997, ER-SDG-4c and ER-SDG-8c control strains. They are the following clones: ER-GAND-12020, ER-GAND 48084, ER-GFD-8044 and ER-GFD-48015.

The strain (deposited, on Jul. 9, 2015, at the CNCM under number I-4998) expressing the STA1 activity derived from *S. cerevisiae* var. *diastaticus* made it possible to obtain rapid but incomplete dextrin hydrolysis kinetics, whereas the strain (I-4899) expressing the GLAA activity derived from *A. niger* made it possible to obtain a dextrin hydrolysis which was satisfactory but had kinetics that were not as good as I-4998.

The strains were pre-propagated on a rich medium overnight at 32° C. The fermentation was carried out at 32° C. The initial pH of the fermentation medium was adjusted to 5.0 without regulation. Urea was added in fermentation (600 ppm). The fermentation medium was then inoculated at a level of 0.5 g equivalent dry matter per kilogram of medium.

The weight loss of the fermentation reactors was measured over time from t=0 to t=66 h.

The results of weight losses obtained during the alcoholic fermentation are presented in FIGS. 17 and 18.

For the ER-GAND series (I-5119 and I-5120), FIG. 17 shows that the new strains make it possible to obtain dextrin hydrolysis that is both as fast as the ER-SDG-4c and ER-SDG-8c strains and as complete as the I-4899 strain, but they are as fast as the I-4997 strain. It can be concluded from this that the production of glucoamylase of *Saccharomyces cerevisiae* var. *diastaticus* still has a stimulating effect on the hydrolytic activity of the *Aspergillus niger* glucoamylase.

For the ER-GFD series (I-5121 and I-5122), FIG. 18 shows that the new strains make it possible to obtain dextrin hydrolysis that is both as fast as the I-ER-SDG4c strain and as complete as the I-4999 strain, but that they are also much faster than the I-4999 strain. It can be concluded from this that the production of glucoamylase of *Saccharomyces cerevisiae* var. *diastaticus* has a stimulating effect on the hydrolytic activity of the *Saccharomycopsis fibuligera* glucoamylase. These strains do nothing but exhibit a combination of the characteristics of the fungal glucoamylase of *Saccharomycopsis fibuligera* and of the glucoamylase of *Saccharomyces cerevisiae* var. *diastaticus* (that is to say with a kinetics profile which is between that of the glucoamylase of *Saccharomycopsis fibuligera* and that of the glucoamylase of *Saccharomyces cerevisiae* var. *diastaticus*), but exhibit an improved kinetics profile with an acceleration of the kinetics. There therefore appears to be a synergistic effect between the glucoamylase of fungal origin and that of *Saccharomyces cerevisiae* var. *diastaticus*.

The invention claimed is:

1. A *Saccharomyces cerevisiae* yeast strain, wherein said yeast strain co-expresses:
   a gene encoding a glucoamylase of fungal origin selected from the group consisting of a glucoamylase of *Aspergillus niger* and a glucoamylase of *Saccharomycopsis fibulifera*; and
   a gene encoding the glucoamylase of *Saccharomyces cerevisiae* var. *diastaticus*,
   wherein the gene encoding the glucoamylase of *Aspergillus niger* comprises the nucleic acid sequence set forth in SEQ ID NO: 1, the gene encoding the glucoamylase of *Saccharomycopsis fibulifera* comprises the nucleic acid sequence set forth in SEQ ID NO: 17, and the gene encoding the glucoamylase of *Saccharomyces cerevisiae* var. *diastaticus* comprises the nucleic acid sequence set forth in SEQ ID NO: 3,
   wherein said *Saccharomyces cerevisiae* yeast strain comprises:
      between 2 and 10 copies of the gene encoding the glucoamylase of fungal origin; and
      between 2 and 10 copies of the gene encoding the glucoamylase of *Saccharomyces cerevisiae* var. *diastaticus*, and
   wherein said *Saccharomyces cerevisiae* yeast strain hydrolyzes liquefied starch extracted from a biomass while at the same time ferments the sugars resulting from hydrolyzed liquefied starch.

2. The *Saccharomyces cerevisae* yeast strain of claim 1, wherein the gene encoding the glucoamylase of *Saccharomyces cerevisiae* var. *diastaticus* encodes a protein comprising the amino acid sequence of SEQ ID NO: 4.

3. The *Saccharomyces cerevisiae* yeast strain of claim 1, wherein the gene encoding the glucoamylase of *Aspergillus niger* comprises the nucleic acid sequence set forth in SEQ ID NO: 1.

4. The *Saccharomyces cerevisiae* yeast strain of claim 3, wherein gene encoding the glucoamylase of *Aspergillus niger* comprises the amino acid sequence of SEQ ID NO: 2.

5. The *Saccharomyces cerevisiae* yeast strain of claim 1, wherein the gene encoding the glucoamylase of fungal origin and the gene encoding the glucoamylase of *Saccharomyces cerevisiae* var. *diastaticus* are integrated into the genome of said yeast.

6. The *Saccharomyces cerevisiae* yeast strain of claim 1, wherein said *Saccharomyces cerevisiae* yeast strain is selected from the strain deposited, on Aug. 6, 2015, at the CNCM [French National Collection of Microorganism Cultures] under I-5005, the strain deposited, on Jul. 9, 2015, at the CNCM under number I-4997, the strain deposited, on Aug. 11, 2016, at the CNCM under number I-5119, the strain deposited, on Aug. 11, 2016, at the CNCM under number I-5120, the strain deposited, on Aug. 11, 2016, at the CNCM under I5121 and the strain deposited, on Aug. 11, 2016, at the CNCM under number I-5122.

7. A *Saccharomyces cerevisiae* yeast strain comprising the nucleic acid sequence of SEQ ID NO: 1 encoding a glucoamylase of *Aspergillus niger* and the nucleic acid sequence of SEQ ID NO: 3 encoding a glucoamylase of *Saccharomyces cerevisiae* var. *diastaticus*, wherein said *Saccharomyces cerevisiae* yeast strain hydrolyzes liquefied starch extracted from a biomass while at the same time ferments the sugars resulting from hydrolyzed liquefied starch.

8. A method for obtaining a *Saccharomyces cerevisiae* yeast strain, said method comprising steps of:
   a) genetically modifying a *Saccharomyces cerevisiae* yeast to co-express a gene encoding a glucoamylase of fungal origin selected from the group consisting of a glucoamylase of *Aspergillus niger* and a glucoamylase of *Saccharomycopsis fibulifera*; and a gene encoding the glucoamylase of *Saccharomyces cerevisiae* var. *diastaticus*, wherein the gene encoding the glucoamylase of *Aspergillus niger* comprises the nucleic acid sequence set forth in SEQ ID NO: 1, the gene encoding the glucoamylase of *Saccharomycopsis fibulifera* comprises the nucleic acid sequence set forth in SEQ ID NO: 17, and the gene encoding the glucoamylase of *Saccharomyces cerevisiae* var. *diastaticus* comprises the nucleic acid sequence set forth in SEQ ID NO: 3, wherein said *Saccharomyces cerevisiae* yeast strain comprises between 2 and 10 copies of the gene encoding the glucoamylase of fungal origin; and between 2 and 10 copies of the gene encoding the glucoamylase of *Saccharomyces cerevisiae* var. *diastaticus*, and wherein said *Saccharomyces cerevisiae* yeast strain hydrolyzes liquefied starch extracted from a biomass while at the same time ferments the sugars resulting from hydrolyzed liquefied starch;
   b) culturing and fermenting the Saccharomyces cerevisiae yeast strain obtained in step a) on a dextrin medium;
   c) selecting the *Saccharomyces cerevisiae* yeast strains having fermentation kinetics at least equal to or greater than the fermentation kinetics, under the same conditions, with the *Saccharomyces cerevisiae* yeast strain deposited, on Jul. 9, 2015, at the CNCM under number I-4999.

9. A process for producing bioethanol from a biomass comprising the steps:
   a) prehydrolyzing and liquefying starch of the biomass to obtain liquefied starch;
   b) contacting the liquefied starch of step a) with the *Saccharomyces cerevisiae* yeast strain of claim 1;
   c) hydrolyzing and fermenting the liquefied starch with said *Saccharomyces cerevisiae* yeast to produce the bioethanol; and
   d) extracting the bioethanol produced in step c).

10. The process of claim 9, wherein said process further comprises adding exogenous glucoamylase enzymes after step b) and/or during step c).

* * * * *

UNITED STATES PATENT AND TRADEMARK OFFICE
CERTIFICATE OF CORRECTION

PATENT NO. : 10,947,519 B2  
APPLICATION NO. : 15/755675  
DATED : March 16, 2021  
INVENTOR(S) : Maud Petit et al.

Page 1 of 1

It is certified that error appears in the above-identified patent and that said Letters Patent is hereby corrected as shown below:

In the Claims

Claim 4, at Column 47, Line 56 should read:
4. The Saccharomyces cerevisiae yeast strain of claim 3, wherein the gene encoding the glucoamylase of Aspergillus niger comprises the amino acid sequence of SEQ ID NO: 2.

Signed and Sealed this
Second Day of November, 2021

Drew Hirshfeld
*Performing the Functions and Duties of the*
*Under Secretary of Commerce for Intellectual Property and*
*Director of the United States Patent and Trademark Office*